(12) United States Patent
Hopper et al.

(10) Patent No.: US 6,803,193 B1
(45) Date of Patent: Oct. 12, 2004

(54) METHODS TO IDENTIFY MODULATORS OF THE MEVALONATE PATHWAY IN STEROL SYNTHESIS

(75) Inventors: Anita K. Hopper, Hershey, PA (US); Nancy C. Martin, Louisville, KY (US); Ann Benko, Palmyra, PA (US); Gabriela Vaduva, St. Louis, MO (US)

(73) Assignee: The Penn State Research Foundation, University Park, PA (US)

( * ) Notice: Subject to any disclaimer, the term of this patent is extended or adjusted under 35 U.S.C. 154(b) by 107 days.

(21) Appl. No.: 09/599,662

(22) Filed: Jun. 22, 2000

Related U.S. Application Data

(60) Provisional application No. 60/199,699, filed on Apr. 26, 2000, and provisional application No. 60/141,516, filed on Jun. 23, 1999.

(51) Int. Cl.[7] .................................................. C12Q 1/68
(52) U.S. Cl. ................................ 435/6; 435/4; 435/29; 435/34; 435/254.2
(58) Field of Search ............................. 435/4, 6, 254.2, 435/29, 34

(56) References Cited

PUBLICATIONS

Boguta et al. Mutation in a new gene MAF1 affects tRNA suppressor efficiency in Saccharomyces cerevisiae. Gene 186:291–296, 1997.*
Arts, et al., "Identification of a nuclear export receptor for tRNA" *Curr Biol* 8:305–314, 1998.
Bach, "Some new aspects of isoprenoid biosynthesis in plants—A review" *Lipids* 30:191–202, 1995.
Bartz, et al., "N6–(Delta 2–isopentenyl)adenosine: Biosynthesis in vitro in transfer RNA by an enzyme purified from *Escherichia coli*" *Biochem Biophys Res Commun* 40:1481–1487, 1970.
Benko, et al., "Competition between a sterol biosynthetic enzyme and the tRNA modification in addtion to changes in the protein synthesis machinery causes altered nonsense suppression" *PNAS* 97:61–66, 2000.
Boguta, et al., "Subcellular locations of MOD5 proteins: mapping of sequences sufficient for targeting to mitochondria and demonstration that mitochondrial and nuclear isoforms commingle in the cytosol" *Mol Cell Biol* 14:2298–2306, 1994.
Brown, et al., "Regression of coronary artery disease as a result of intensive lipid–lowering therapy in men with high levels of apolipoprotein B" *B Engl J Med* 323:1289–98, 1990.
Brown and Goldsteins, "Multivalent feedback regulation of HMG CoA reductase, a control mechanism coordinating isoprenoid synthesis and cell growth" *J Lipid Res.* 21:505–517, 1980.
Carlson and Botstein, et al., "Two differentially regulated mRNAs with different 5' ends encode secreted with intracellular forms of yeast invertase", *Cell* 28:145–154, 1982.

Chen, et al., "PPQ, a novel protein phosphatase containing a Ser+Asn–rich amino–terminal domain, is invovled in the regulation of protein synthesis" *Eur. J. Biochem* 218:689–699, 1993.
Chijiwa and Linscheer's (Chijiwa and Linscheer, "Effect of intraluminal pH on cholesterol and oleic acid absorption from micellar solutions in rat" *Am J. Physiol* 246:G492–G499, 1984.
Dihanich, et al., "Isolation and characterization of MOD5, a gene required for isopentenylation of cytoplasmic and Mittochondrial tRNAs of *Saccharomyces cerevisiae*" *Mol Cell Biol* 7:177–184, 1987.
Donald, et al., "Effects of overproduction of the catalytic domian of 3–hydroxy–3–methylglutaryl coenzyme A reductase on squalene synthesis in *Saccharomyces cerevisiae*" *Appl Environ Microbiol* 63:3341–3344, 1997.
Endo, et al., "Beneficial effects of dietary intervention on serum lipid and apolipoprotein levels in obese children" *Am J Dis Child* 146:303–305, 1992.
Endo, et al., "Oxygenated cholesterols as ligands for cytosolic–nuclear tumor promoter binding protein: yakkasteroids" *Biochem Biophys Res Commun* 194:1529–35, 1993.
Endo, "The discovery and development of HMG–CoA reductase inhibitors" *J Lipid Res* 33:1569–1582, 1992.
Endres et al., "Role of peroxynitrite and neuronal nitric oxide synthase in the activation of poly(ADP–ribose) synthetase in a murine model of cerebral ischemia–reperfusion" *Neurosci Lett.* 248:41–41, 1998.
Frantz and Gilbert, "A novel yeast gene product, G4p1, with a specific affinity for quadruplex nucleic acids" *J. Biol Chem* 270:20692–20697, 1995.
Gibbs and Oliff, "The potential of farnesyltransferase inhibitors as cancer chemotherapeutics" *Annu Rev Pharmacol Toxicol.* 37:143–66, 1997.
Gietz, et al., "Improved method for high efficiency transformation of intact yeast cells" *Nucleic Acids Res* 20:1425, 1992.
Gillman, et al., "MODS translaion initiation sites determine N6–isopentenyladenosine modification of mitochondrial and cytoplasmic tRNA" *Mol Cell Biol* 11:2382–2390, 1991.
Goldstein and Brown, "Regulation of the mevalonte pathway" *Nature* 343:425–430, 1990.
Hinnebusch and Liebman, in *The molecular and cellular biology of the yeast Saccharmyces: Genomic dynamics, protein synthesis and energetics* eds. Broach, et al. "Protein Synthesis and Translational Control in *Saccharomyces cerevisiae*" [Cold Spring Harbor Lab Press, Plainview, NY] vol. 1, pp. 627–735, 1991.

(List continued on next page.)

*Primary Examiner*—James Ketter
*Assistant Examiner*—David Lambertson
(74) *Attorney, Agent, or Firm*—Medlen & Carroll, LLP

(57) ABSTRACT

An assay for the detection of substances agonistic or antagonistic to the mevalonate pathway are disclosed.

2 Claims, 10 Drawing Sheets

OTHER PUBLICATIONS

Hopper, et al., "Processing of intervening sequences: a new yeast mutant which fails to excise intervening sequences from precursor tRNAs" *Cell* 19:741–751, 1980.

Janssen and Möller, "Elongation factor 1 β γ from Artemia. Purification and properties of its subunits" *Eur J Biochem* 171:119–129, 1988.

Kinzy, et al., "Multiple genes encode the translation elongation factor EF–1γ in *Saccharomyces cerevisiae*" *Nucleic Acids Res* 22:2703–2707, 1994.

Kline, et al., "N6–($\Delta^2$–Isopentenyl) adenosine. Biosynthesis in transfer ribonucleic acid in vitro" *Biochemistry* 8:4361–4371, 1969.

Laten, et al., "Isopentenyladenosine deficient tRNA from an antisuppressor mutant of Saccharomyces cerevisiae" *Nucleic Acids Res* 5:4329–4342, 1978.

Laufs et al., "Upregulation of endothelial nitric oxide synthase by HMG CoA reductase inhibitors" *Circulation* 97:1129–35, 1998.

Liu, et al., "Construction of a GAL1–regulated yeast cDNA expression library and its application to the identification of genes whose overexpression causes lethality in yeast" *Genetics* 132:665–673, 1992.

Lund and Dahlberg, "Proofreading and aminoacylation of tRNAs before export from the nucleus" *Science* 282:2082–2085, 1998..

Martin and Hopper, "Isopentenuylation of both cytoplasmic and mitochondrial tRNA is affected by a single nuclear mutation" *J Biol Chem* 257:10562–10565, 1982.

McCloskey and Nishimuta, "Modified Nucleosides in Transfer RNA" *Acc. Chem. Res.* 10:403–410, 1977.

McKnight et al., "Selection of Functional cDNAs by complementation in yeast," *PNAS* 80:4412–4416, 1983.

Najarian et al., "DNA Sequence and Transcript Mapping of MOD5: Features of the s' Region which Suggest Two Translational Starts," *Mol. Cell. Biol.* 7:185–191, 1987.

Nash, "Meeting National Cholesterol Education Goals in Clinical Practice–A Comparison of Lovastatin and Fluvastatin in Primary Prevention," *Am. J. Cardiol.* 78(SuppL. 6A):26:31, 1996.

Nasmyth and Tatchell, "The structure of transposable yeast mating type loci" *Cell* 19:753–764, 1980.

Ono et al., "Nonsense Mutations in the can1 Locus of Saccharomyces cerevisiae," *J. Bacteriology* 154:1476–1479, 1983.

Rasmussen and Culbertson, "Analysis of yeast trimethylguanosine–capped RNAs by Midwestern blotting" *Gene* 182:89–96, 1996.

Rasse–Messenguy and Fink, "Temperature–sensitive nonsense suppressors in yeast" *Genetics* 75:459–464, 1973.

Rine, "Gene overexpression in studies of *Saccharomyces cerevisiae*" *Method Enzymol* 194:239–251, 1991.

Rosenbaum and Gefter, "$\Delta^2$–Isopentenylpyrophosphate: Transfer Ribonucleic Acid $\Delta^2$–Isopentenyltransferase from *Escherichia coli*. Purification and properties of the enzyme" *J. Biol Chem* 247:5675–5680, 1972.

Rothstein, "Targeting, Disruption, replacement, and allele rescue: integrative DNA transformation in yeast" *Methods Enzymol* 194:281–301, 1991.

Sanger, et al., "DNA sequencing with chain–terminating inhibitors" *Proc. Natl Acad Sci USA* 74:5463–5467, 1977.

Sarkar, et al., "Nuclear tRNA aminocylation and its role in nuclear export of endogenous tRNAs in *Saccharomyces cerevisiae*" *PNAS* 96:14366–14371, 1999.

Sarkar and Hopper, "tRNA nuclear export in *Saccharomyces cerevisiae*: in situ hybridization anlaysis" *Mol Biol Chell* 9:3041–3055, 1998.

Senapathy and Jacob, "Identification and purification of tRNAs containing N6–(delta 2–isopentenyl) adenosine using antibodies specific for N6–(delta–isopentenyl) adenosine" *J Biol Chem* 256:11580–11584, 1981.

Simos, et al., "The yeast protein Arc1p binds to tRNA and functions as a cofactor for the methionyl–and glutamyl–tRNA synthetases" *EMBO J* 15:5437–5448, 1996.

Sinensky, et al., "Differential inhibitory effects of lovostatin on protein isoprenylation and sterol synthesis" *J Biol Chem* 265:19937–19941, 1990.

Sinha et al., "Polymer support oligonucleotide synthesis XVIII1.2: use of β–cyanoethyl–N, N–dialkylamino–/N–morppholono phosphoramidite of deoxynucleosides for the synthesis of DNA fragments simplifying deprotection and isolation of the final product," *Nucleic Acids Res.* 12:4539–4557, 1984.

Song, et al., "Elongation factor EF–1 alpha gene dosage alters translational fidelity in *Saccharomyces cerevisiae*" *Mol Cell Biol* 9:4571–4575, 1989.

Stansfield, et al., "The products of the SUP45 (eRF1) and SUP35 genes interact to mediate translation termination in *Saccharomyces cerevisiae*" *EMBO J* 14:4365–4373, 1995.

Stansfield and Tuite, "Polypeptide chain termination in *Saccharomyces cerevisiae*" *Curr Genet* 25:385–395, 1994.

Tanimoto et al., "Inhibitory activity to protein prenylation and antifungal activity of zaragozic acid D3, a potent inhibitor of squalene synthase produced by the fungus, *Mollisia* sp SANK 10294" *J. Antibiot (Tokyo)* 51:428–431, 1998.

Vincent, et al.,"the yeast translational allosuppressor, SAL6: a new memeber of the PP1–like phosphatase family with a long serine–rich N–terminal extension" *Genetics* 138:597–608, 1994.

Voet and Voet, in *Biochemistry* "Lipid Metabolism," John Wiley & Sons, Inc. Chapter 23 pp. 645–657, 1990.

Ward, "Single–step purification of shuttle vectors from yeast for high frequency back–transformaation into *E.coli*" *Nucleic Acids Res* 18:5319, 1990.

Whelan et al., "The CANI locus of *Saccharomyces cerevisiae*: fine–structure analysis and forward mutation rates" *Genetics* 91:35–51, 1979.

Woolford and Warner, in *The molecular and cellular biology of the yeast Saccharomyces: Genomic dynamics, protein synthesis and energetics* eds., Broach, et al. "The Ribosome and Its Synthesis" [Cold Spring Harbor Lab Press, Plainview, NY] vol. 1, pp. 587–626, 1991.

Zoladek et al., "Mutations altering the mitochondrial–cytoplasmic distribution of Mod5p implicate the actin cytoskeleton and mRNA 3'ends and/or protein synthesis in mitochondrial delivery" *Mol Cell Biol.* 15:6884–6894, 1995.

* cited by examiner

YEp24; ☐, yeast sequences of vector YEp24; ■, E. coli sequences of vector YEp24; —, insert of yeast genomic DNA; ▨, 1.8 kb BglII fragment used as a probe and fragment in YEpMOD5(1.8) and YCpMOD5(1.8). B, BamHI; C. ClaI; E, EcoRI; G, BglII; M, SmaI; S, SalI; V, PvuII.

METHODS TO IDENTIFY MODULATORS OF THE MEVALONATE PATHWAY IN STEROL SYNTHESIS

PRIORITY

This application for patent under 35 U.S.C. 111(a) claims priority, under 35 U.S.C. § 119(e), to Provisional Applications Serial No. 60/141,516 (filed on Jun. 23, 1999) and No. 60/199,699 (filed on Apr. 26, 2000); wherein said Provisional Applications were filed under 35 U.S.C. 111(b).

STATEMENT REGARDING FEDERAL SPONSORSHIP

This invention was made in part with government support under grants MCB9506810 and MCB9828216 from the National Science Foundation. The government has certain rights in the invention.

FIELD OF THE INVENTION

This invention generally relates to a novel assay for the screening of compounds that are agonistic or antagonistic to the mevalonate pathway and sterol and cholesterol synthesis. In selected embodiments this assay incorporates colorimetric, growth, and immunological methods for high throughput screening of compounds.

BACKGROUND

A finely tuned mechanism regulates the biosynthesis of mevalonate, the precursor of isoprenoid groups that are incorporated into more than a dozen classes of end products. These include: sterols, especially cholesterol, involved in membrane structure; haem A and ubiquinone, involved with electron transport; dolichol, required for glycoprotein synthesis; isopenentyladenine, present in some transfer RNAs; and intercellular messengers, such as cytokines in plants, farnesylated mating factors in fungi, juvenile hormones in insects and steroid hormones in animals. Interest in the regulatory importance of mevalonate was heightened by the discovery that growth-regulating $p21^{ras}$ proteins (encoded by ras proto-oncogenes and oncogenes) and nuclear envelope proteins, are covalently attached to farnesyl residues. These farnesyl residues, in turn, anchor said proteins to cell membranes. Inhibition of mevalonate synthesis prevents farnesylation of these proteins and blocks cell growth. To ensure constant production of the multiple isoprenoid compounds at all stages of growth, cells must precisely regulate mevalonate synthesis while avoiding over accumulation of potentially toxic products such as cholesterol. (Goldstein and Brown, "Regulation of the mevalonate pathway" *Nature* 343:425–430, 1990).

The ability to regulate flux through the mevalonate pathway (FIG. 1) is of medical importance because inhibitors of this pathway have been used to treat hypercholesterolemia and, consequently, to diminish the risk of heart attack. (Endo, "The discovery and development of HMG-CoA reductase inhibitors" *J Lipid Res* 33:1569–1582, 1992). Alteration of the pathway also affects the function of oncogenes (Reviews: Gibbs and Oliff, "The potential of farnesyltransferase inhibitors as cancer chemotherapeutics" *Annu Rev Pharmacol Toxicol.* 37:143–66, 1997. The mevalonate pathway is an important target for many areas of therapeutic research and application. For example, HMG-CoA reductase catalyzes the rate-limiting step of the mevalonate pathway (Voet and Voet, *Biochemistry* Wiley, New York, 1990); therefore, inhibitors of this reductase have been developed for administration to patients with hypercholesterolemia in an attempt to lower their blood cholesterol levels (Endo, et al., "Oxygenated cholesterols as ligands for cytosolic-nuclear tumor promoter binding protein: yakkasteroids" *Biochem Biophys Res Commun* 194:1529–35, 1993). Data reveals that the "statin" class (eg., compactin and lovastatin; see FIG. 1) of reductase inhibitors are reasonably safe and somewhat effective in lowering total cholesterol levels and preventing the progression and reducing the occurrence of coronary disease events (Brown, et al., "Regression of coronary artery disease as a result of intensive lipid-lowering therapy in men with high levels of apolipoprotein B" *N Engl J Med* 323:1289–98, 1990; Endo, et al., "Beneficial effects of dietary intervention on serum lipid and apolipoprotein levels in obese children" *Am J Dis Child* 146:303–305, 1992; Nash, et al., "Meeting national cholesterol education goals in clinical practice—a comparison of lovastatin and fluvastatin in primary prevention" *Am J Cardiol.* 78 (Suppl. 6A):26–31, 1996, but more progress needs to be made in the development of therapies that are more effective.

As an indication of the breadth of potential therapeutic effect regulators of the mevalonate pathway can have, the statins, in addition to regulating cholesterol levels, also stimulate nitric oxide production (Endres et al., "Role of peroxynitrite and neuronal nitric oxide synthase in the activation of poly(ADP-ribose) synthetase in a murine model of cerebral ischemia-reperfusion" *Neurosci Lett.* 248:41–4, 1998; Laufs et al., "Upregulation of endothelial nitric oxide synthase by HMG CoA reductase inhibitors" *Circulation* 97:1129–35, 1998), have antiproliferative affects on some types of cancer cells (Lee et al., "Inhibition of the 3-Hydroxy-3-methylglutaryl-coenzyme A reductase pathway induces p53-independent transcriptional regulation of $p21^{waf1/cip1}$ in human prostate carcinoma cells" J. Biol. Chem. 273: 10618–10623, 1998) and have immunosuppressive affects. Zaragozic acid inhibits the enzyme activity of squalene synthase which is the first step of the pathway committed solely to sterol biosynthesis, but appears not to be currently used in the clinical setting. Zaragozic acid D3 inhibits farnesyl-protein transferase and, therefore, protein prenylation as well (Tanimoto et al., "Inhibitory activity to protein prenylation and antifungal activity of zaragozic acid D3, a potent inhibitor of squalene synthase produced by the fungus, Mollisia sp SANK 10294" *J Antibiot (Tokyo)* 51:428–431, 1998).

A screen for compounds affecting various steps of the mevalonate pathway, therefore, could identify potential therapeutics for treatment of hypercholesterolemia and other pathological conditions associated with sterol metabolism in addition to compounds which may inhibit oncogene protein prenylation and farnesynelation. Moreover, the availability of a screen for flux through the sterol pathway could be useful for predicting undesirable side effects of drugs designed to treat other illnesses. Furthermore, since the mevalonate pathway is common to most organisms, compounds that regulate the mevalonate pathway may have uses beyond medicine such as agriculture and pest control. Therefore, what is needed is an efficient, flexible, high-throughput assay to screen for agents that are agonistic or antagonistic to mevalonate pathway function.

SUMMARY OF THE INVENTION

The present invention relates to an assay designed to detect flux in the melvonate pathway. In one embodiment the assay is a plate based assay incorporating the yeast strain *Saccharomyces cerevisiae*. Although it is not intended that the present invention be limited to a specific mechanism, it is believed that the modification of tRNA by Mod5p is in competition with flux through the mevalonate pathway. This competition results from both Mod5p and Erg20p using the same substrate, dimethylallyl-PP (FIG. 1). Mod5p catalyzes the transfer of an isopetenyl moiety to an adenosine generating $i^6A$ at position 37 of some tRNAs. This modification affects the function of the tRNA in translation and may be measured by monitoring nonsense suppression. As shown in FIGS. 2 & 5F, two yeast strains have been generated that possess limiting cytosolic levels of Mod5p. When there is increased flux through the mevalonate pathway, in one example, by overproduction of Erg20p (FIG. 1), there is less $i^6A$ modification of tRNA (FIG. 3). This decreases the proliferation of cells which grow on media that will support strains expressing normal levels of Erg20p. See, FIG. 2. Such a highly sensitive assay can differentiate as little as a two-fold difference in the level of $i^6A$ modification of tRNA. (Benko, et al., "Competition between a sterol biosynthetic enzyme and the tRNA modification in addition to changes in the protein synthesis machinery causes altered nonsense suppression" PNAS 97:61–66, 2000).

Increased cytosolic levels of Mod5p cause a different phenotype easily assayed by growth on media lacking lysine (Zoladek et al., "Mutations altering the mitochondrial-cytoplasmic distribution of Mod5p implicate the actin cytoskeleton and mRNA 3' ends and/or protein synthesis in mitochondrial delivery" Mol Cell Biol. 15:6884–6894, 1995), thereby, providing a means for selecting reagents that decrease flux through the pathway. In one embodiment of the present invention, therefore, yeast growth on particular media can provide an index for both increases and decreases in mevalonate pathway flux. The assays contemplated by the present invention are efficient, inexpensive and provide new methods for screening drugs that alter the clinically significant mevalonate pathway.

It is not intended that the present invention be limited to the identification of compounds for only to a specific therapeutic application. However, in selected embodiments, compounds that regulate the mevalonate pathway may be beneficial in: (1) screening for new drugs to treat hyperlipidemias and other disorders in sterol metabolism such as Addison's disease and Cushing's syndrome; (2) screening for drugs that inhibit the function of farnesylated and prenylated oncogene products; (3) monitoring other drugs for possible side effects in sterol metabolism; (4) identification of yeast mutants with altered sterol metabolism; (5) screening for agents that alter plant physiological processes such as, for example, photosynthesis, cell growth, respiration, architecture and defense against pathogen attack (e.g., antibiotics and antifungals).

The present invention relates to a flexible, high throughput screen for agents that are agonistic or antagonistic to mevalonate pathway function. The present invention is not limited to any particular high throughput assay. Many high throughput assays are contemplated by the present invention. For example, in one embodiment, the present invention contemplates visually scoring plates. In another embodiment, the present invention contemplates culturing cells in microtiter plates, performing the assay, lysing the cells and generating a readout of said cell lysates via a spectrophotometer. In another embodiment the present invention contemplates reading the cells in a flow cytometer to detect changes in cell color and in cell growth. In another embodiment, the present invention contemplates measuring (in one example by scintillation) radiation generated by $H^3$-tritium as an index to determine cell growth. In preferred embodiments, the assay may be performed manually or with the use of automation and robotics for any or all steps in the aforementioned procedures.

The present invention relates to yeast strains engineered to provide detectable read-outs for compounds that are agonistic or antagonistic to the mevalonate pathway. In a preferred embodiment, the yeast strains are ALB1 (genotype: MATα mod5-M2 SUP7 ade2-1 can1-100 leu2-3, -112 lys1-1 lys2-1 trp1 ura3-1), ALB8 (genotype: MATα SUP7 can1-100 ade2-1 leu2-3, -112 lys1-1 lys2-1 trp1 mod5::TRP1 ura3-1::MOD5) and MT8-1D or MD14A with YCfmod5-m2KR6 plasmid for a lysine based assay.

It is not intended that the present invention be limited to the screening of any particular compound or class of compounds. Proteins, lipids, carbohydrates, glycoproteins, lipoproteins, synthetic compounds, compounds contained in combinatorial libraries or compounds and agents already being used as therapeutics may be screened by the present assay. Moreover, the screening of known therapeutics according to the present invention will reveal, heretofore, unknown side effects associated with the modulation of the mevalonate pathway.

It is not intended the present invention be limited to any particular protocol to quantitate or qualitate the assay. In selected embodiments, for example, the assay output may be measured visually, colorimetrically, fluorescently, by immunoblot, by radio-immunoassay or by HPLC. In a one embodiment, anti-$i^6A$ antibody is used to detect $i^6A$ production in cells treated with a compound. In a preferred embodiment, a Western blot is used to detect the presence of $i^6A$. Quantitation is not limited to any particular method. Quantitation may be made by densitometer, chemilumiinescence, and radiography.

The present invention contemplates a composition comprising yeast with the relevant genotype of: SUP7 ade2-1 can1-100 leu2-3 mod5-M2 and designated ALB1. The present invention further contemplates a composition wherein the yeast ALB1 is a strain of Saccharomyces cerevisiae. Still further, the present invention contemplates a composition comprising yeast with the relevant genotype of: SUP7 can1-100 ade2-1 leu2-3 mod5::TRP1 ura3-1::MOD5 and designated ALB8. Even still further, the present invention contemplates a composition wherein the yeast ALB8 is a strain of Saccharomyces cerevisiae. Even further still, the present invention contemplates a composition comprising the yeast strain ALB1 wherein the genotype further comprises: MATα mod5-M2 SUP7 ade2-1 can1-100 leu2-3, -112 lys1-1 lys2-1 trp1 ura3-1. Even still further, the present invention contemplates a composition wherein the yeast ALB1 is a strain of Saccharomyces cerevisiae. Even further still, the present invention contemplates a composition comprising yeast with the relevant genotype of:: MATα SUP7 can1-100 ade2-1 leu2-3, -112 lys1-1 lys2-1 trp1 mod5::TRP1 ura3-1::MOD5 and designated ALB8. Even further still, the present invention contemplates a composition of claim 7 wherein the yeast is Saccharomyces cerevisiae.

The present invention contemplates a method, comprising: a) providing: i) a test compound, ii) a growth media formulated to allow scoring of nonsense suppression in yeast, and iii) modified yeast cells derived from wild type yeast cells, wherein said modified yeast cells express reduced cytosolic levels of Mod5p, or its homolog, as compared to said wild type yeast cells, and wherein said modified yeast cells comprise a gene with a nonsense mutation and a suppressor tRNA gene coding for a tRNA modified with isopentenyl adenosine by Mod5 or its homolog; b) exposing a portion of said modified yeast cells to said test compound and said growth media to create a treated portion and an untreated portion; and c) measuring for growth of said treated portion.

The present invention also contemplates a measuring of step which comprises examining the color of said yeast cells of said treated portion.

Additionally, the present invention contemplates a measuring of step which comprises comparing said treated portion with said untreated portion, wherein said untreated portion is exposed to said growth media in the absence of said test compound.

The present invention contemplates a method, comprising: a) providing: i) a test compound, ii) a growth media lacking adenine, and iii) modified yeast cells derived from wild type yeast cells, wherein said modified yeast cells express reduced cytosolic levels of Mod5p as compared to said wild type yeast cells, and wherein said modified yeast cells comprise an ADE gene having a nonsense mutation and a gene coding for a nonsense suppressor tRNA; b) exposing a portion of said modified yeast cells to said test compound and said growth media to create a treated portion and an untreated portion; and c) measuring for growth of said treated portion.

The present invention also contemplates a method, comprising: a) providing: i) a test compound, ii) a growth media lacking adenine, and iii) modified yeast cells derived from wild type yeast cells, wherein said modified yeast cells express reduced cytosolic levels of Mod5p as compared to said wild type yeast cells, and wherein said modified yeast cells comprise an ADE gene having a nonsense mutation and a SUP7 gene coding for a tRNA; b) exposing a portion of said modified yeast cells to said test compound and said growth media to create a treated portion and an untreated portion; and c) measuring for growth of said treated portion.

The present invention also contemplates a method, comprising: a) providing: i) a test compound, ii) a growth media lacking arginine and comprising a canavanine salt, and iii) modified yeast cells derived from wild type yeast cells, wherein said modified yeast cells express reduced cytosolic levels of Mod5p as compared to said wild type yeast cells, and wherein said modified yeast cells comprise a CAN1 gene having a nonsense mutation and a gene coding for a nonsense suppressor tRNA; b) exposing a portion of said modified yeast cells to said test compound and said growth media to create a treated portion and an untreated portion; and c) measuring for growth of said treated portion.

The present invention also contemplates a method, comprising: a) providing: i) a test compound, ii) a growth media lacking arginine and comprising a canavanine salt, and iii) modified yeast cells derived from wild type yeast cells, wherein said modified yeast cells express reduced cytosolic levels of Mod5p as compared to said wild type yeast cells, and wherein said modified yeast cells comprise a CAN1 gene having a nonsense mutation and a SUP7 gene coding for a tRNA; b) exposing a portion of said modified yeast cells to said test compound and said growth media to create a treated portion and an untreated portion; and c) measuring for growth of said treated portion.

Additionally, the present invention contemplates a method wherein said gene coding for said nonsense suppressor tRNA is selected from the group consisting of SUP7 and SUP11.

The present invention further contemplates a method comprising: a) providing i) one or more compounds, ii) a first yeast cell line designated ALB1; ii) a second yeast cell line designated ALB8; b) contacting a portion of said cells from i) said first yeast cell line and ii) said second yeast cell line, with said one or more said compounds, so as to create treated portions and untreated portions or cells; and, c) comparing said treated cells with said untreated cells. Even further, the present invention contemplates that the method of comparison of said treated or untreated cells may be by color and cell growth (i.e., the amount of cell division).

The present invention further contemplates a method comprising: a) providing i) one or more compounds and ii) a yeast cell line selected from a group consisting of yeast strains designated ALB1 and ALB8; b) contacting a portion of said cells from said yeast cell line with said one or more said compounds, so as to create treated portions and untreated portions of cells; and, c) i) comparing said treated cells with said untreated cells. The present invention further contemplates the comparison of treated and untreated cells by color and by cell growth.

DEFINITIONS

To facilitate understanding of the invention, a number of terms are defined below.

"Genotype" shall be defined as the genetic makeup of an organism as encoded in its DNA.

"Relevant genotype" shall be defined as specific genes that, if expressed, have impact on the investigation under way.

A "nonsense suppressor tRNA" is meant to indicate one of several known suppressor tRNAs. For example, SUP7-1 codes for an altered tRNA that is one of several efficient tyrosine-inserting UAA suppressors. (H. Laten et al., Nucleic Acids Res. 5:4329 (1978)). Indeed, SUP7 (and SUP11 for that matter) can suppress the lys2-1 nonsense allele (as well as other nonsense mutations). The LYS2 gene encodes an enzyme involved in the biosynthesis of lysine. Mutations in this gene prevent growth on media lacking exogenous lysine.

As used herein, the term "scoring of nonsense suppression in yeast" refers to determining the level of suppression due to translation though the nonsense codon in mRNA relative to a control sample wherein said control sample comprises reduced or absent translation through the nonsense codon in mRNA because of differences in suppressor tRNA.

As referred to herein, cells with the mod5-M2 allele (strain ALB1 projected in FIG. 2) contains a mutation at codon 12 preventing the initiation of Mod5p-II translation (and allow only Mod5p-I production) have about 50% of the SUP7 pool modified resulting in intermediate levels of suppression. These cells show intermediate growth on canavanine and on media lacking adenine.

Figure 5A:
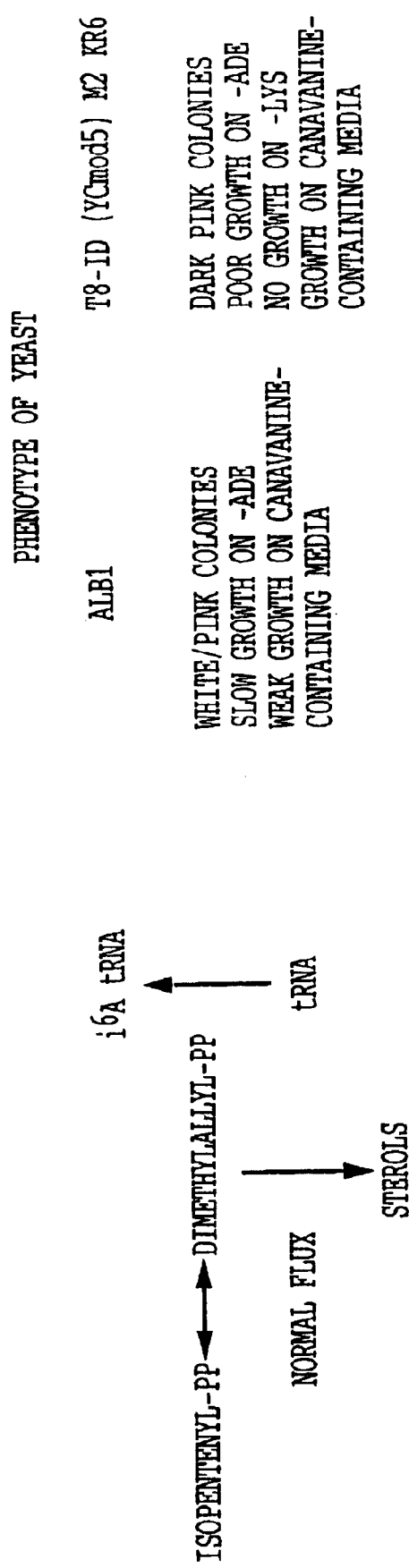
FIG. 5A presents the growth characteristics for ALB1 cells and T8-1D cells (with YCfmod5-M2,KR6) under conditions of normal flux through the sterol biosynthesis pathway.
Figure 5B:
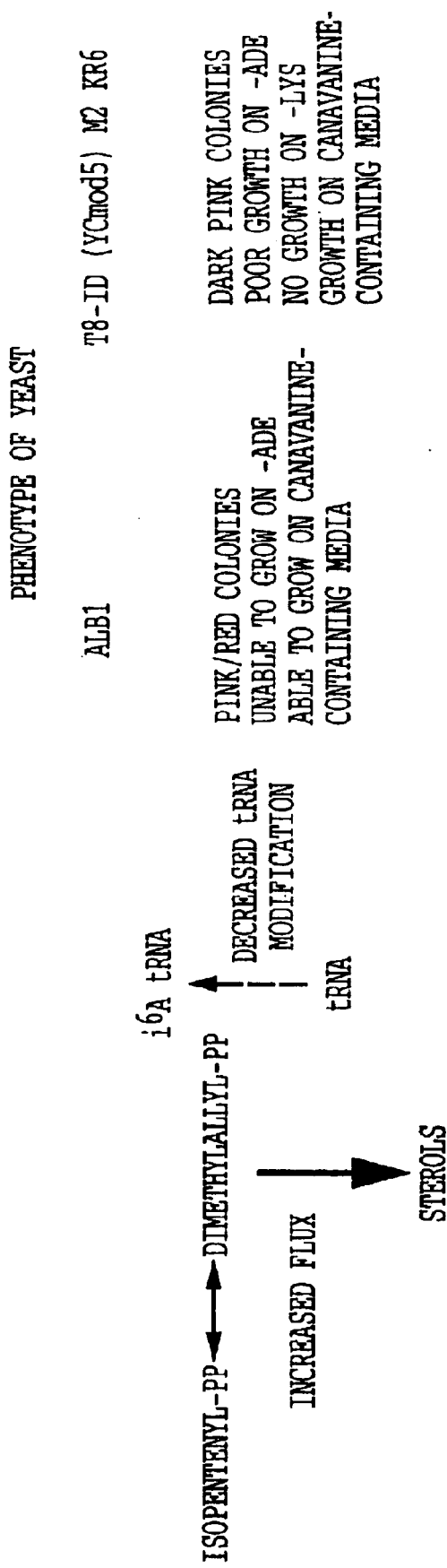
FIG. 5B presents the growth characteristics for ALB1 cells and T8-1D cells (with YCfmod5-M2,KR6) under conditions such that flux through the sterol biosynthesis pathway is increased.
Figure 5C:
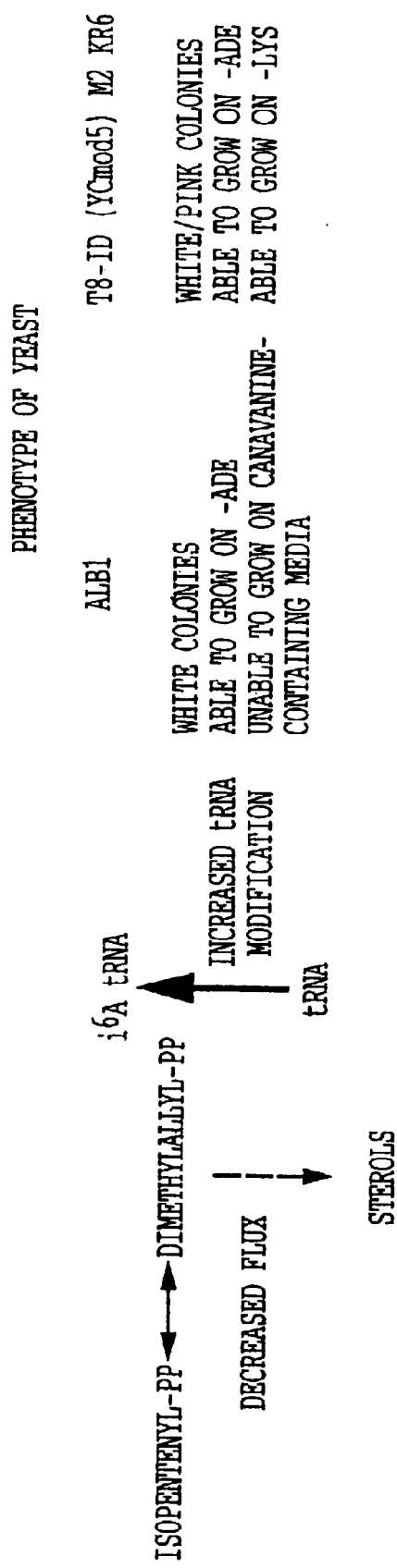
FIG. 5C presents the growth characteristics for ALB1 cells and T8-1D cells (with YCfmod5-M2,KR6) under conditions such that flux through the sterol biosynthesis pathway is decreased.
Figure 6:
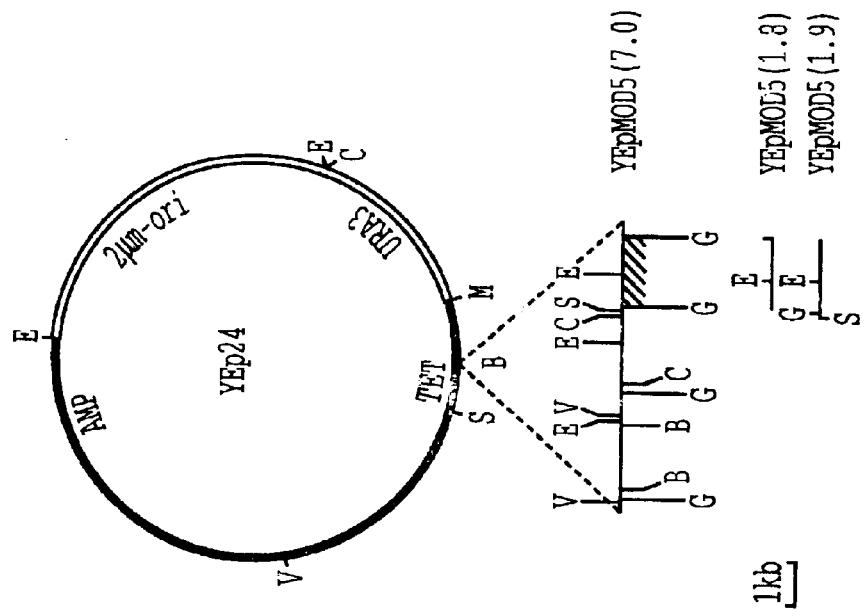
FIG. 6 presents a restriction map of YEpMOD5(7.0) and subclones YEpMOD5(1.8) and YEpMOD5(1.9). Numbers in parentheses indicate size of insert. See, Dihanich, et al., "Isolation and characterization of MOD5, a gene required for isopentenylation of cytoplasmic and mitochondrial tRNAs of *Saccharomyces cerevisiae*" *Mol Cell Biol* 7:177–184, 1987).

As referred to herein, cells with the mod5-M2KR6 allele (T8-1D with Ycfmod5-M2KR6 as projected in FIG. 5) have a very small cytosolic pool of Mod5p and the cells are unable to grow in the absence of lysine.

Yeast strain "ALB1" is defined as a substantially pure population of yeast with the genotype of: MATα mod5-M2 SUP7 ade2-1 can1-100 leu2-3, -112 lys1-1 lys2-1 trp1 ura3-1 and the relevant genotype of: SUP7 ade2-1 can1-100 leu2-3-112 mod5-M2. The yeast may be of the species *Saccharomyces cerevisiae*.

Yeast strain "ALB8" shall be defined as a substantially pure population of yeast with the genotype of: MATα SUP7 can1-100 ade2-1 leu2-3, -112 lys1-1 lys2-1 trp1 mod5::TRP1 ura3-1::MOD5. The yeast may be of the species *Saccharomyces cerevisiae*.

Yeast strain "T8-1D" shall be defined as a substantially pure population of yeast with the genotype of: MATα SUP11 ade2-1 leu2-3, -112 mod5-1 lys2-1 his4-519 ura 3-1. The yeast may be of the species *Saccharomyces cerevisiae*.

As used herein, CAN1 refers to a sequence encoding an arginine permease that allows the uptake of the arginine analog canavanine. Canavanine interferes with the process of translation and cells cannot grow in its presence. Therefore, cells with wild-type CAN1 are sensitive to canavanine, but cells with the mutant can 1-100, that does not encode a properly functioning permease, are resistant to canavanine and can grow in its presence. See, Bun-Ichiro Ono, et al., "Nonsense Mutations in the can1 Locus of *Saccharomyces cervisiae*", Journal of Bacteriology, June 1983, pp. 1476–1479.

As used herein, ADE2 refers to a sequence which encodes an enzyme involved in the synthesis of adenine. Cells with ade2-1 turn red in color and fail to grow on defined medium lacking adenine (Ade), whereas cells producing functional Ade2p can grow on such medium (Ade+) and are white. Cells with the ade2-1 allele and sufficient i6A-modified suppressor tRNA can grow in the absence of exogenous adenine and generate white colonies on rich medium, whereas cells with insufficient i6A-modified tRNA are unable to grow in the absence of exogenous adenine and generate red colonies on rich medium. Cells with intermediate levels of i6A modified tRNA have intermediate phenotypes in colony color and intermediate rates of growth in the absence of exogenous adenine.

As used herein a, "substantially deficient adenine growth media" refers to a culture media that, in one embodiment, has less than 20 mg/L of adenine while in a preferred embodiment has less than 5 mg/L of adenine.

"Wild type" shall be defined as the genomic makeup of an organism (the genotype) before modifications have been made. In other words, it is the parent strain of the organism.

The term "binding interaction" when used in relation to RNA shall be defined as the ability of two or more macromolecules to bind to each other (e.g., to produce an aggregate). The present invention makes no limit on the stringency of the binding interaction so long as the interaction can be detected by methods known to those practiced in the art (e.g., by Western blot, coimmunoprecipitation, spectrophotometry, colorimetric assay, etc.).

The term "homology" when used in relation to proteins refers to a degree of similarity. There may be partial homology or complete homology (i.e., identity). A partially similar sequence is one that may partially inhibit a similar sequence from performing its function (e.g., enzymatic, binding, etc) in vivo or in vitro and is referred to using the functional term "substantially homologous." The inhibition function of the substantially similar sequence may be examined using an enzymatic assay, a binding assay or other assay designed to measure the particular function of the substantially similar protein. A substantially homologous proteins may compete for or interfer with a homolog and inhibit its function (e.g., the binding or enzymatic function). This is not to say that conditions of low stringency are such that non-specific interaction is permitted; low stringency conditions require that the interaction be a specific (i.e., selective) interaction.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 ug/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "purified" or "to purify" refers to the removal of contaminants from a sample. The present invention contemplates purified compositions (e.g. the ALB1 and ALB8 stains of S. cerevisiae).

As used herein, the term "substantially purified" refers to the removal of a significant portion of the contaminants of a sample to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are "functional" if they contain a binding region (i.e., a region having affinity for another molecule) and such binding can take place (i.e., the binding region functions, albeit with perhaps lower affinity than that observed for the full-length protein). Such "functional portions" of the gene product are typically greater than 50 amino acids in length, and more typically greater than 100 amino acids in length. "Functional portions" may also be "conserved portions" of the protein. The alignment of the yeast and human gene products (described herein) permit one skilled in the art to select conserved portions of the protein (i.e., those portions in common between yeast and man) as well as unconserved portions (i.e., those portions unique to either yeast or man). The present invention contemplates conserved portions 20 amino acids in length or greater, and more typically greater than 50 amino acids in length.

As used herein the term "portion" when in reference to an oligonucleotide sequence (as in "a portion of a given sequence") refers to fragments of that sequence. The fragments may range in size from four base residues to the entire oligonucleotide sequence minus one base. More typically, such portions are 15 nucleotides in length or greater. Again, such portions may be conserved portions (see FIG. 8). On the other hand, such portions may be unique portions of the gene.

"Compound" refers to any chemical entity, pharmaceutical, drug, and the like that can be used to treat or prevent a disease, illness, sickness, or disorder of bodily function. Compounds comprise both known and potential therapeutic compounds. A compound can be determined to have therapeutic potential by screening, e.g., using the screening methods of the present invention. A "known therapeutic compound" refers to a therapeutic compound that has been shown (e.g., through animal trials or prior experience with administration to humans) to be effective in such treatment or prevention.

"Antibody" shall be defined as a glycoprotein produced by B cells that binds with high specificity to the agent (usually, but not always, a peptide), or a structurally similar agent (e.g., $i^6A$), that generated its production (e.g., the $i^6A$ antibody). Antibodies may be produced by any of the known methodologies [Current Protocols in Immunology (1998) John Wiley and Sons, Inc., N.Y.] and may be either polyclonal or monoclonal.

"Antigen" shall be defined as a protein, glycoprotein, lipoprotein, lipid or other substance that is reactive with an antibody specific for a portion of the molecule.

The terms "immunoprecipitate", "immunoprecipitated", "immunoprecipitation" refer to the use of antibody to take an antigen out of solution by precipitation.

The term "affinity purification" refers to the use of an antibody to separate its antigen or a portion thereof from a mixture of other molecules because of affinity for the antigen.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g., a fluorescent microscope).

"Staining" shall be defined as any number of processes known to those in the field that are used to better visualize, distinguish or identify a specific component(s) and/or feature(s) of a cell or cells.

"RIA" or "radioimmunoassay" shall be defined as an assay wherein antibody is used to detect antigen and thereafter quantitated with radioisotopes.

"Immunoabsorbant" and "immunoaffinity" shall be defined as binding antigen with antibody reactive to said antigen. The antibody or the antigen may be bound to a solid or semi-solid substrate.

"Western blot" shall be defined as an assay comprising antigen that is detected by antibodies reactive to the antigen after the antigen has been at least partially separated from contaminants by, for example, electrophoresis.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Heterologous DNA" sequence refers to a nucleotide sequence which is not endogenous to the cell into which it is introduced. Heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced and which contains some modification relative to the naturally-occurring sequence.

"Morphology" shall be defined as the visual appearance of a cell or organism when viewed with the eye, a light microscope, a confocal microscope or an electronmicroscope, as appropriate. Morphology shall include, but is not limited to, cell shape, cell appearance and cell color.

"Patient" shall be defined as a human or other animal, such as a guinea pig or mouse and the like.

GENERAL DESCRIPTION OF THE INVENTION

This invention generally relates to a novel assay for the screening of compounds that are agonistic or antagonistic to the mevalonate pathway and sterol and cholesterol synthesis. In selected embodiments this assay incorporates colorimetric, growth, biochemical (e.g., HPLC) and immunological methods for high through-put screening of compounds.

Baker's yeast *Saccharomyces cerevisiae* are single celled eukaryotes used extensively as model organisms. This model system provides for the facile manipulations of yeast genes, availability of the complete genomic sequence of baker's yeast, and identification of numerous yeast genes which directly correlate with known human disease genes. One fundamental discovery that has become clear from the use of this model system is that many physiologically significant regulatory pathways and proteins are highly conserved among all eukaryotes. Importantly, mammalian homologues of many yeast proteins are known to be important in regulating cell physiology, including the mevalonate pathway. Therefore, these model systems have been effectively utilized for the rapid identification and functional characterization of compounds that may be of use as therapeutics in higher eukaryotes. Thus yeast is well suited as a model system not only for the elucidation of basic cell biology but also for large-scale screening of compounds which specifically target cell growth.

I. Assay Development

The *Saccharomyces cerevisiae* protein Mod5p catalyzes the addition of an isopentenyl group to adenosine ($i^6A$) at position 37 of the anticodon loop of some tRNAs (Kline, et al, "N6-(delta-2-isopentenyl)adenosine. Biosynthesis in transfer ribonucleic acid in vitro" *Biochemistry* 8:4361–4371, 1969; Bartz, et al., "N6-(Delta 2-isopentenyl) adenosine: biosynthesis in vitro in transfer RNA by an enzyme purified from *Escherichia coli*" *Biochem Biophys Res Commun* 40:1481–1487, 1970; Rosenbaum and Gefter, "Delta 2-isopentenylpyrophosphate: transfer ribonucleic acid 2-isopentenyltransferase from *Escherichia coli*. Purification and properties of the enzyme" *J Biol Chem* 247:5675–5680, 1972; McCloskey and Nishimura, *Acc. Chem. Res.* 10:403–410, 1977; Dihanich, et al., "Isolation and characterization of MOD5, a gene required for isopentenylation of cytoplasmic and mitochondrial tRNAs of *Saccharomyces cerevisiae*" *Mol Cell Biol* 7:177–184, 1987). There are two isoforms of Mod5p, Mod5p-I and Mod5p-II, which differ in the site of their translation initiation codon and in their distribution in the cell. Mod5p-I is translated starting at codon one of the MOD5 ORF and is localized to mitochondria and the cytoplasm. Mod5p-II, translated from codon twelve of the MOD5 ORF, is located in the nucleus and the cytoplasm (Gillman, et al., "MOD5 translation initiation sites determine N6-isopentenyladenosine modification of mitochondrial and cytoplasmic tRNA" *Mol Cell Biol* 11:2382–2390, 1991; Boguta, et al., "Subcellular locations of MOD5 proteins: mapping of sequences sufficient for targeting to mitochondria and demonstration that mitochondrial and nuclear isoforms commingle in the cytosol" *Mol Cell Biol* 14:2298–2306, 1994).

Over-expression of Erg20p causes a decrease in $i^6A$ tRNA-mediated suppression in yeast and an approximately 70% decrease in $i^6A$ modification of tRNA. These effects are most likely due to the loss of Mod5p substrate to Erg20p. The data demonstrate the dependence of tRNA processing upon changes in components of the sterol pathway. The data also indicate that, at least in yeast, Erg20p may also catalyze a rate-limiting step in sterol biosynthesis. Hence, the tRNA and the sterol biosynthetic pathways are in apparent competition and a delicate balance in protein levels is required to maintain proper functioning of translation and mevalonate metabolism.

The $i^6A$ modification promotes the efficiency of SUP7 or SUP11 tRNA in cytosolic suppression of UAA nonsense mutations by the insertion of tyrosine (Laten, et al., "Isopentenyladenosine deficient tRNA from an antisuppressor mutant of *Saccharomyces cerevisiae*" *Nucleic Acids Res* 5:4329–4342, 1978). Cells possessing only Mod5p-I have limiting cytosolic amounts of isozyme and changes in the subcellular distribution and/or the activity of this isozyme alter nonsense suppression. Hence genetic screens/selections based on nonsense suppression can identify cells with altered cytosolic Mod5p-I activity (Zoladek, et al., "Mutations altering the mitochondrial-cytoplasmic distribution of Mod5p implicate the actin cytoskeleton and mRNA 3' ends and/or protein synthesis in mitochondrial delivery" *Mol Cell Biol* 15:6884–6894, 1995).

Applicants employed the genetic strategy of using over expression to perturb a pathway (Rine, "Gene overexpression in studies of *Saccharomyces cerevisiae*" *Methods Enzymol* 194:239–251, 1991) and developed a protocol for the selection of cells with lower than normal levels of cytosolic Mod5p-I activity. Using this strategy Applicants were able to sample the entire yeast genome and identify genes that, when overexpressed, lead to lower than normal, levels of cytosolic Mod5p-I activity.

As a result of that screen, Applicants have identified two categories of genes. The first category includes genes that affect nonsense suppression via alteration of the protein synthetic machinery. Applicants' studies suggest that the yeast gene product encoded by YDL219w may function in protein synthesis and that the translation elongation factor EF1-γ may function in translational proofreading. SAL6 and ARC1, with previously established effects on protein synthesis, were also recovered.

Figure 1:
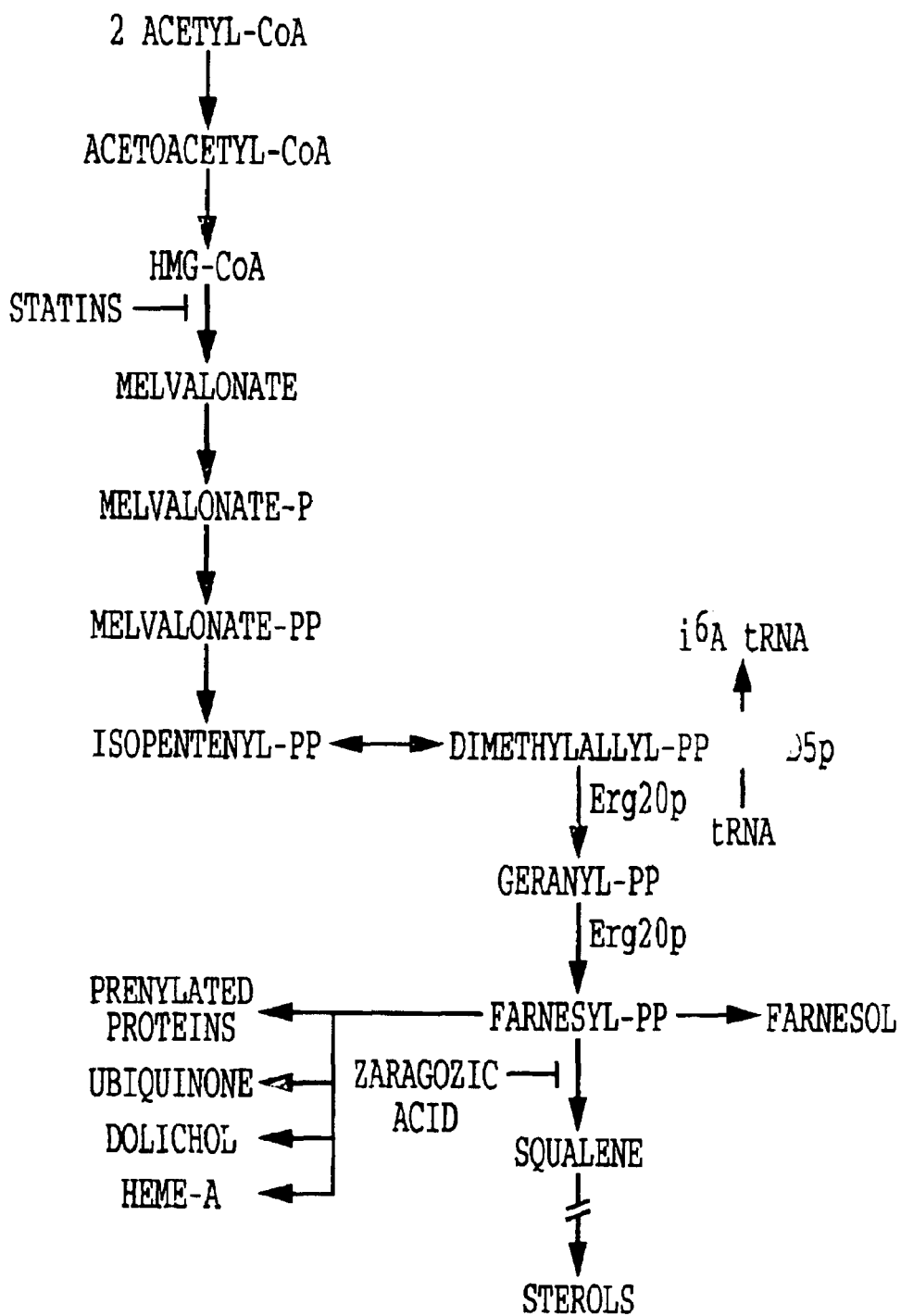
FIG. 1 shows the mevalonate pathway.

The second category includes ERG20, involved in sterol biosynthesis. The mevalonate pathway generates sterols, prenylated proteins, heme A, dolichol, ubiquinone and the substrate required for isopentenylation of tRNAs (FIG. 1). Both Mod5p and Erg20p use the same substrate, dimethylallyl pyrophosphate (DMAPP). Recovery of ERG20 coupled with subsequent biochemical assays demonstrating a reduction of $i^6A$ on tRNA is most easily explained by a model in which Mod5p and Erg20p compete for a limited pool of DMAPP. When more DMAPP is used to make sterols, less is available for modification of tRNA and a reduction in the efficiency of nonsense suppression results. Thus, Applicants have demonstrated that the tRNA biosynthetic pathway and the sterol biosynthetic pathway are in apparent competition for substrate and that Erg20p and Mod5p must be balanced to optimally maintain the protein synthetic machinery. A practical consequence is that it should be possible to adapt the selection the applicants developed to assess the effect of mutations and/or drugs that change the distribution of DMAPP between the sterol pathway and the tRNA biosynthetic pathway.

Applicants interest in the distribution of sorting isozymes led to the design of a screen for gene products that function in the subcellular distribution of Mod5p or affect its ability to modify cytosolic tRNAs. Applicants anticipated the discovery of genes affecting transcription of MOD5 and/or tRNAs, nuclear export of tRNA, and the translation process, (in addition to those involved in protein distribution). Three gene products, Sal6p, Tef4p and YDL219w, may affect nonsense suppression via function in protein translation and Arc1p could play a role in nuclear export of tRNA. No gene products affecting MOD5 or tRNA transcription or Mod5p-I subcellular distribution were uncovered. Rather, ERG20, important to sterol biosynthesis, was discovered.

Sal6p/Ppq1p is a serine-threonine protein phosphatase very similar to mammalian phosphatase PP1 (Vincent, et al., "The yeast translational allosuppressor, SAL6: a new member of the PP1-like phosphatase family with a long serine-rich N-terminal extension" Genetics 138:597–607, 1994; Chen, et al., "PPQ, a novel protein phosphatase containing a Ser+ Asn-rich amino-terminal domain, is involved in the regulation of protein synthesis" Eur J Biochem 218:689–699, 1993). Multiple copies of SAL6 cause antisuppression of nonsense mutations (Vincent, et al., "The yeast translational allosuppressor, SAL6: a new member of the PP1-like phosphatase family with a long serine-rich N-terminal extension" Genetics 138:597–607, 1994) and the sal6-1 allele acts as an allosuppressor (Vincent, et al., "The yeast translational allosuppressor, SAL6: a new member of the PP1-like phosphatase family with a long serine-rich N-terminal extension" Genetics 138:597–607, 1994; Stansfield and Tuite, "Polypeptide chain termination in Saccharomyces cerevisiae" Curr Genet 25:385–395, 1994). Yeast cells containing a disrupted PPQ1 gene exhibit a slowed translation rate and hypersensitivity to inhibitors of protein synthesis (Chen, et al., "PPQ, a novel protein phosphatase containing a Ser+ Asn-rich amino-terminal domain, is involved in the regulation of protein synthesis" Eur J Biochem 218:689–699, 1993). These findings suggest a role for Sal6p in the regulation of the fidelity of translation (Vincent, et al., "The yeast translational allosuppressor, SAL6: a new member of the PP1-like phosphatase family with a long serine-rich N-terminal extension" Genetics 138:597–607, 1994; Chen, et al., "PPQ, a novel protein phosphatase containing a Ser+ Asn-rich amino-terminal domain, is involved in the regulation of protein synthesis" Eur J Biochem 218:689–699, 1993).

Tef4p is the gamma subunit of elongation factor 1 (EF-1). Eukaryotic EF-1 functions in delivering incoming tRNAs to the ribosome and is composed of at least three subunits. EF-1α binds GTP and then the proper aminoacyl-tRNA and positions the aminoacyl tRNA in the ribosomal A site. Subsequently, GTP is hydrolyzed to GDP and EF-1β catalyzes the exchange of GDP for GTP to restore EF-1α to its initial state (Kinzy, et al., "Multiple genes encode the translation elongation factor EF-1 gamma in Saccharomyces cerevisiae" Nucleic Acids Res 22:2703–2707, 1994; Hinnebusch and Liebman, in "The molecular and cellular biology of the yeast Saccharomyces: Genomic dynamics, protein synthesis and energetics" eds. Broach, et al. [Cold Spring Harbor Lab Press, Plainview, N.Y.] Vol. 1, pp. 627–735, 1991). The exact function of EF-1δ has not been determined; however, in Artemia salina this subunit was observed to enhance the function of EF-1β catalysis. In the same study EF1-γ was found to interact with cell membranes and tubulin suggesting that it might mediate the association of the translational machinery with the cell framework (Janssen and Möller, "Elongation factor 1 beta gamma from Artemia. Purification and properties of its subunits" Eur J Biochem 171:119–129, 1988).

In bacteria the EF-1 counterpart functions in translational proofreading. Incorrectly inserted aminoacyl tRNAs can be removed prior to GTP hydrolysis and prior to the departure of EF-1α from the ribosome (Hinnebusch and Liebman, in "The molecular and cellular biology of the yeast Saccharomyces: Genomic dynamics, protein synthesis and energetics" eds. Broach, et al. [Cold Spring Harbor Lab Press, Plainview, N.Y.] Vol. 1, pp. 627–735, 1991). If the yeast EF-1 serves a similar function as the . bacterial counterpart, it is unlikely that the a subunit participates in this function as extra copies of the genes encoding EF-1α decrease fidelity (i.e., they enhance suppression of nonsense mutations; Song, et al., "Elongation factor EF-1 alpha gene dosage alters translational fidelity in Saccharomyces cerevisiae" Mol Cell Biol 9:4571–4575, 1989). Applicants show that over-expression of Tef4p reduces nonsense suppression and therefore it is possible that it is the EF1-γ subunit that functions in EF-1 proofreading.

ORF YDL219w is predicted to code for a 150 amino acid protein with no significant homology to any characterized protein. However two lines of evidence indicate that this protein may function in the translation process. First, the gene possesses an intron [(Saccharomyces Genome Database, http://genome-www.stanford.edu/cgi-bin/dbrun)]. As introns are rare in yeast other than for approximately half of the genes encoding ribosomal proteins (Woolford and Warner, in "The molecular and cellular biology of the yeast Saccharomyces: Genomic dynamics, protein synthesis and energetics" eds. Broach, et al. [Cold Spring Harbor Lab Press, Plainview, N.Y.] Vol. 1, pp. 587–626, 1991), the presence of the intron is suggestive of a role in translation. Second, Applicants show that over expression of YDL219w affects tRNA-mediated nonsense suppression.

Arc1p, or G4p1, was originally discovered as a quadruplex nucleic acid binding protein (Frantz and Gilbert, "A novel yeast gene product, G4p1, with a specific affinity for quadruplex nucleic acids" J Biol Chem 270:20692–20697, 1995). Subsequently, Arc1p was demonstrated to bind tRNA and to complex with methionyl and glutamyl tRNA synthetases (Simos, et al., "The yeast protein Arc1p binds to tRNA and functions as a cofactor for the methionyl- and glutamyl-tRNA synthetases" EMBO J 15:5437–5448, 1996. Recent studies have shown that aminoacylation is important for tRNA nuclear export (Lund and Dahlberg, "Proofreading and aminoacylation of tRNAs before export from the nucleus" Science 282:2082–2085, 1998; Sarkar, et al., "Nuclear tRNA aminoacylation and its role in nuclear export of endogenous tRNAs in Saccharomyces cerevisiae" PNAS 96:14366–14371, 1999). Moreover, Simos et al. (Simos, et al., "The yeast protein Arc1p binds to tRNA and functions as a cofactor for the methionyl- and glutamyl-tRNA synthetases" EMBO J 15:5437–5448, 1996) uncovered ARC1 by synthetic interactions with Los1p, the yeast tRNA exportin (Arts, et al., "Identification of a nuclear export receptor for tRNA" Curr Biol 8:305–314, 1998; Sarkar and Hopper, "tRNA nuclear export in Saccharomyces cerevisiae: in situ hybridization analysis" Mol Biol Cell 9:3041–3055, 1998).

Thus, it is possible that over-expression of Arc1p interferes with the appropriate nucleus cytosol distribution of tRNA. Alternatively, over-expressed Arc1p could interfere with the interaction of tRNA and ribosomes. Incubation of tRNA$^{Met}$ with large amounts of Arc1p in vitro, resulted in the creation of supershifted complexes in a gel mobility assay, indicative of higher-order complexes (Simos, et al., "The yeast protein Arc1p binds to tRNA and functions as a cofactor for the methionyl- and glutamyl-tRNA synthetases" *EMBO J* 15:5437–5448, 1996). Perhaps, large quantities of cellular Arc1p complexes with tRNA, preventing the tRNA from functioning normally in translation.

Figure 4:
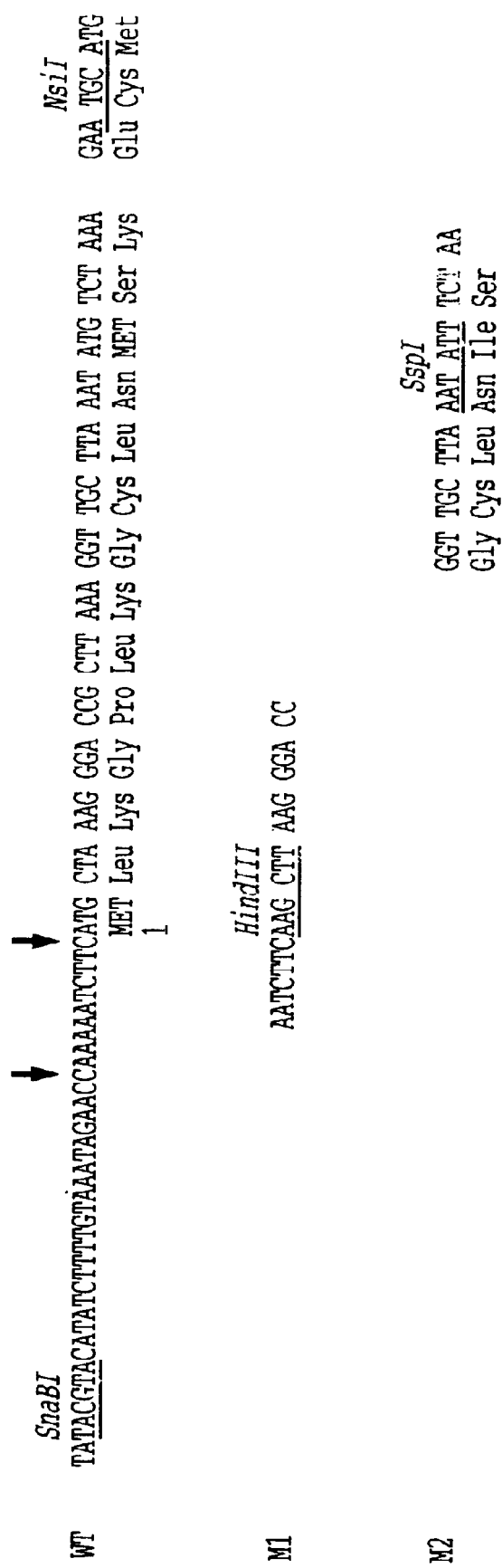
FIG. 4 presents selected mutations introduced into the MOD5 gene and oligonucleotides. See, Gillman et al., "MOD5 translation initiation sites determine N6-isopentenyladenosine modification of mitochondrial and cytoplasmic tRNA", *Mol Cell Biol* 11:2382–2390.

It is contemplated that mutations may be introduced into the MOD5 gene and oligonucleotides used in mutagenesis. FIG. 4 (SEQ ID NOS: 1–5) presents the nucleotide sequence of the MOD5 gene from two nucleotides 5' of the SnaBI site upstream of the open reading frame codon 14, followed by the sequence in the area of the first NsiI site. The DNA sequences of oligonucleotides M1 and M2 are shown below the corresponding wild-type (WT) sequence. Restriction endoculease recognition sites are underlined and indicated above the sites. Encoded amino acids are in three-letter code below codons. The first two methionine codons are indicated by capital letters. The M2 oligonucleotide encodes the only amino acid change in MOD5 (Met to Ile); all other changes become part of the 5' noncoding portion of the gene, Arrows show positions of 5' ends of MOD5 transcripts.

The mevalonate pathway generates sterols, prenylated proteins, heme A, dolichol, ubiquinone and isopentenyl tRNAs. Inhibitors of HMG-CoA reductase, catalyzing a rate-limiting step of the pathway, have been developed for administration to patients with hypercholesterolemia (Goldstein and Brown, "Regulation of the mevalonate pathway" *Nature* 343:425–430, 1990. The "statin" class (e.g., compactin and lovastatin) of reductase inhibitors are safe and effective in lowering total cholesterol levels and preventing the progression and reducing the occurrence of coronary disease events (Endo, "The discovery and development of HMG-CoA reductase inhibitors" *J Lipid Res* 33:1569–1582, 1992; Brown, et al., "Regression of coronary artery disease as a result of intensive lipid-lowering therapy in men with high levels of apolipoprotein B" *N Eng J Med* 323:1289–1298, 1990; Nash, "Meeting national cholesterol education goals in clinical practice—a comparison of lovastatin and fluvastatin in primary prevention" *Am J Cardiol* 78: Suppl. 6A:26–31, 1996. Zaragozic acid inhibits squalene synthetase catalzying the first step of the pathway committed solely to sterol biosynthesis, but appears not to be currently used in the clinical setting. A novel type of zaragozic acid, ZAD3, also inhibits farnesyl protein transferase and, therefore, protein prenylation as well (Tanimoto, et al., "Inhibitory activity to protein prenylation and antifungal activity of zaragozic acid D3, a potent inhibitor of squalene synthase produced by the fungus, Mollisia sp sank 10294" *J Antibiot* 51:428–431, 1998). There appears to be no drug in current clinical use that affects solely cholesterol biosynthesis without affecting other farnesyl-PP-derived products.

Applicants have demonstrated that increased levels of an enzyme of the sterol biosynthetic pathway can be assessed indirectly simply by colony color and/or growth on particular media because changes in nonsense suppression occur. Thus, additional mutations and/or drugs that affect the pathway could be identified by a modification of the screening protocol Applicants describe. The effect of prospective new regulators of pathway enzymes on the suppressor ability of a strain with the ALB1 genotype (mod5-M2 SUP7 can1-100 ade2-1) could be assessed by adding them to canavanine-containing or adenine-lacking media and monitoring cell growth. If the presence of a substance enhances colony growth on canavanine or deters colony formation on media lacking adenine or causes red colony color to develop, in comparison to the growth/color observed on media without the test substance, then the substance may be increasing the flow of DMAPP through the mevalonate pathway and decreasing tRNA modification. Likewise, using the mod5-M2,KR6 allele Applicants have previously shown (Zoladek, et al. "Mutations altering the mitochondrial-cytoplasmic distribution of Mod5p implicate the actin cytoskeleton and mRNA 3' ends and/or protein synthesis in mitochondrial delivery" *Mol Cell Biol* 15:6884–6894, 1995) that increased cytosolic Mod5p activity results in acquisition of the ability to grow on media lacking lysine. Therefore, compounds that decrease use of DMAPP by the sterol pathway may also be easily assessed. In this way, potential enhancers and inhibitors of the mevalonate pathway could be initially screened for their efficacy quickly and inexpensively.

II. Assay Applications

The Mevalonate Pathway

The mevalonate pathway produces isoprenoids that are vital for diverse cellular functions, ranging from cholesterol synthesis to growth control. Several mechanisms for feedback regulation of low-density-lipoprotein receptors and of two enzymes involved in mevalonate biosynthesis ensure the production of sufficient mevalonate for several endproducts. Manipulation of this regulatory system could be useful in treating certain forms of cancer as well as heart disease.

In animal cells, a finely tuned metabolic feedback mechanism involving transcriptional and post-transcriptional inputs maintains a pool of mevalonate pathway intermediates essential for cell survival in addition to maintaining cholesterol homeostasis. Cholesterol, the bulk end product of the pathway in sterologenic tissues, exerts transcriptional control on sequential activities in the mevalonate pathway, principally those catalyzed by HMG CoA synthetase, HMG CoA reductase and farnesyl pyrophosphate synthase. HMG CoA reductase is the rate-limiting enzyme of mevalonate biosynthesis as well as the most highly regulated enzyme in this series. The multivalent regulation of HGM CoA reductase integrates activities at the transcriptional, posttranscriptional and post-translational levels. Sterol-mediated regulation of transcription, the dominant regulatory site in sterologenic tissues, is mediated through the sterol regulatory element (SRE), a promoter-enhancer octanucleotide sequence located in the 5' flanking region of the reductase gene.

Cholesterol

Since cholesterol is present in all tissues of vertebrates and some invertebrates—crustacea (crab, shrimp) and higher mollusks (e.g., squid)—it follows that carnivores ingest appreciable quantities of cholesterol. Not only food but also the bile and, to a small extent, the intestine contribute to the cholesterol available for absorption. Experimental work suggests that the internal cholesterol pool is heterogeneous because biliary cholesterol is more effectively absorbed than dietary cholesterol.

In rats, biliary cholesterol is primarily absorbed in the proximal half of the small bowel, but dietary cholesterol is absorbed in the distal half. Although these observations suggest much better absorption of endogenous that exogenous cholesterol, actually only slightly more endogenous than exogenous cholesterol is absorbed. Several investigators using an isotopic-equilibrium method, concluded that in normal human subjects the maximal capacity for absorbing dietary cholesterol in about 300 to 500 mg/day. Others, using combined chemical and isotope balance methods, have shown that 30 to 40% of dietary cholesterol is absorbed in most adults over an intake range of 40 mg/day to more than 2 g/day.

Although some disagree about the percentage of absorption, all investigators agree that only part of the cholesterol of both origins is absorbed. This in itself is a remarkable fact if one considers the different conditions for cholesterol absorption for the two sources of cholesterol. Bile cholesterol, for example, consists of unesterfied cholesterol already solubilized in mixed bile salts (BS) phospholipids (PL) micelles. Exogenous cholesterol is not water soluble and is not absorbed an in FA ester. Pancreatic cholesterol esterase, activated by BS, is capable of splitting cholesterol ester into the free sterol and fatty acid (FA), but this is a rather slow process compared to the hydrolysis of triglycerides (TG). Free cholesterol is dissolved in the oil phase and into micelles. When the oil phase disappears, cholesterol precipitates slowing down the rate of absorption.

That cholesterol is only absorbed via micellar solubilization may explain the relatively poor absorption of exogenous cholesterol in healthy subjects, but it does not explain why endogenous cholesterol is poorly absorbed also. It is most likely that cholesterol absorption from micelles slows down considerably when monoglycerides (MG), FA, and PL have disappeared from the micelle because their rate of absorption is much faster and BS micelles alone are poor detergents. Chijiwa and Linscheer's (Chijiwa and Linscheer, "Effect of intraluminal pH on cholesterol and oleic acid absorption from micellar solutions in rat" *Am J Physiol* 246:G492–G499, 1984) observation that absorption rates of cholesterol are much higher at the lower pH of the duodenum and proximal jejunum than at the higher pH in the distal half of the small bowel suggests that this may be a contributing factor.

The physiological malabsorption of cholesterol (related to its very low solubility in water) is essential for the intestinal excretion mechanism of cholesterol. Cholesterol is also the substrate for BS synthesis, but reabsorption of BS is highly efficient and the amount of BS excreted in feces is not the main excretory pathway of cholesterol.

The normal intake of cholesterol (200 to 600 mg/day) accounts for only a small fraction of the total cholesterol transported, and because its contribution to the pool is small, no saturation will be apparent for the absorption of dietary cholesterol. Although individual responses of blood cholesterol show marked variations when animals and humans are exposed to increased amounts of dietary cholesterol and some may even show no clear charge, the majority will react with an increase in concentration of blood (and tissue) cholesterol. Apparently no adequate compensatory mechanism exists for the augmented absorption by the reduction of endogenous cholesterol synthesis and for the increased excretion via the bile.

Although an increase dietary cholesterol load may increase serum cholesterol by approximately 15%, most serum cholesterol is the product of endogenous synthesis. In view of the limited effect of dietary cholesterol on total serum cholesterol, therefore, a method for screening compounds regulating endogenous de novo cholesterol synthesis is paramount.

Cancer

Elucidation of the genes involved in cellular proliferation and the underlying mechanisms that promote and inhibit cell cycle progression has required the use of simple, genetically manipulatable model systems. The present invention makes possible the ability to screen for compounds that may have chemotherapeutic use without the need to run complex genetic experiments. It also allows for the screening of compounds that are agonistic or antagonistic to a pathway known to influence tumor growth and survival.

Mutant ras oncogenes and alterations in the mitogenic signaling pathways that they regulate are associated with a wide variety of solid tumors and leukemias for which existing chemotherapeutics have limited utility. Of the possible approaches to inhibit Ras function, much attention has focused on a postranslational modification, farnesylation, which is required for the subcellular localization of Ras to the plasma membrane and is critical to Ras cell-transforming activity. Inhibitors of the enzyme that catalyzes Ras farnesylation, farnesyl-protein transferase (FPTase), have been developed as chemotherapeutics thereby showing the potential use of this approach for the development of anti-cancer drugs (Gibbs and Oliff, "The potential of farnesylatransferase inhibitors as cancer chemotherapeutics" *Annu. Rev. Pharmacol. Toxical.* 37:143–166, 1997). However, the identification of these agents by current technologies is a slow and tedious process. The present invention will allow for the high-through put screening of compounds that have potential use as chemotherapeutics.

Obesity

The present invention is also useful for the screening of compounds that may be beneficial in the control of obesity. Metabolic flux in the mevalonic acid pathway depends on the activity of 3-hydroxy-3-methylglutaryl coenzyme A (HMG-CoA) reductase, which regulates the first part of the pathway and the overall synthesis of cholesterol (Goldstein and Brown, "Regulation of the mevalonate pathway" *Nature* 343:425–430, 1990). Experiments with inhibitors of this enzyme have shown that protein prenylation is preserved under conditions that drastically reduce the biosynthesis of cholesterol, suggesting there are regulatory mechanisms acting downstream HMG-CoA reductase to preserve the supply of FPP and GGPP, the isoprenoids used in protein isoprenylation (Sinensky, et al., "Differential inhibitory effects of lovastatin on protein isoprenylation and sterol synthesis" *J Biol Chem* 265:19937–19941, 1990). GGPP is over expressed in multiple tissues of the ob/ob mouse. It is also expressed in increased amounts during adipocyte differentiation in culture. Mammalian GGPP synthase catalyzes the synthesis of FPP and GGPP, the two isoprenoids that take part in protein prenylation. This suggests that this enzyme, by itself or in combination with FPP synthase, serves as a favored point for regulation of prenyl group production for protein prenylation. This protein appears highly regulated during adipogenesis and is overexpressed in an animal model of obesity. In this regard, compounds that regulate the mevalonate pathway may be useful in the regulation of downstream products of the pathway that influence adipogenesis and obesity.

Plants

The present invention is also useful for the detection and identification of compounds that may be agonistic or antagonistic to the mevalonate pathway in plants. As in yeast, dimethylallyl pyrophosphate (DMAPP) is the substrate of both isopentenyladenasine ($i^6A$) synthesis and a multitude of down stream products from the mevalonate pathway. The mevalonate pathway in plants is responsible for the production of compounds that are necessary for photosynthesis (carotenoids, chlorophylls, phylloquinone, plastoquinone), respiration (ubiquinone, cytechrome a), membrane architecture (sterols and triterpenoids), regulation of growth and development (gibberellic acids, abscisic acid, brassinosteriods, certain cytokinins), defense against pathogen attack (numerous isoprenoid phytoalexins), exchange of signals and prenylation of proteins (allowing for membrane targeting and cell cycle regulation) (Bach, "Some new aspects of isoprenoid biosynthesis in plants—A review" *Lipids* 30:191–202, 1995). Once compounds are found that regulate the mevalonate pathway, they may be further screened by conventional assays known to those in the art for use in various capacities. In this regard, the present invention is useful for the screening of compounds that may be beneficial as regulators of photosynthesis, membrane integrity, plant growth (e.g., fertilizers) and protection (e.g., insecticides, fungicides, antimicrobials and antivirals).

Fungi

Fungi are single celled living forms of life which inhabit the land, air and waters of the earth. They are more highly developed than bacteria and viruses. It is estimated that there are over 500,000 different species. Fungi have existed on earth hundreds of millions of years and, quite remarkably, have experienced little genetic change during that period of time. Viable fungi can grow from spores which have been dormant for thousands of years, such as has been observed in spores which were found in Egyptian tombs.

Single fungal cells can only be seen under the microscope, but a colony of these cells makes a visible presence in the form of mushrooms, toad stools and molds on food or elsewhere. While plants, animals and humans are alive and well, the fungi around them are usually unable to overcome the natural defense mechanisms which higher forms of life possess. Once death of the living organism has occurred, however, the fungi become the principle undertakers and managers. They are instrumental in reducing all that has ever lived into the molecules from which they were assembled.

Unfortunately, though, there is one exception to this simple balanced equation of life and death and that is that the fungi can also attack living cells. At its most simplistic perspective, one has many fungi entering the intestinal tract, the nose and lungs, and organs exposed to the outside world. Though animals generally do not develop an infection from such intrusions, some persons might contract a fungal infection such as "athlete's foot" or "ring worm" on the skin.

At the opposite extreme is the patient with AIDS who faces major life-threatening fungal infections because the immune system has lost its ability to protect the body from organisms which invade the body, such as fungi. In between these extremes are fungal infections associated with diseases such as diabetes, cancer as welt as conditions which include intra- and inter-specific cross infections. Two groups of fungi that are of medical importance are yeast and molds. Both are nearly ubiquitous and species of both can cause infections in mammals. Common ailments attributed to fungi are yeast infections and various fungal skin infections. More severe medical conditions can occur if internal infections arise, e.g., after surgery.

Additionally, fungi produce mycotoxins. Mycotoxins are biologically active substances that have evolved as a protective mechanism for the fungus. Some mycotoxins have become useful to humans. Antibiotics, such as penicillin, are examples. However, many mycotoxins can be harmful or deadly. Fungal infections, therefore, are not only limited to the site of infection, but, through the production of mycotoxins, can adversely affect the entire organism. For example, mycotoxins have been linked to cancer. Therefore, even if the fungal infection is cleared, the patient may still suffer long term consequences as a result of the infection.

This invention contemplates the screening of compounds that can be useful as anti-fungal agents for both animals and plants. To be useful as an anti-fungal therapeutic, the desired compound would have to be toxic to the fungus without causing undue negative effects on the patient. The invention, by virtue of the ubiquitousness of the mevalonate pathway, provides a screen where compounds that are potential anti-fungal therapeutics can be identified. Additionally, the present invention will be useful in the identification of compounds that may be used to eliminate yeast as an infectious agent.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, and microbial culture and transformation (e.g., electroporation, lipofection). Generally enzymatic reactions and purification steps are performed according to the manufacturer's specifications. The techniques and procedures are generally performed according to conventional methods in the art and various general references (see, generally, Sambrook i) et al. Molecular Cloning: A Laboratory Manual, 2d ed. (1 989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference.

Oligonucleotides can be synthesized on an Applied BioSystems oligonucleotide synthesizer [for details see Sinha et al., Nucleic Acids Res. 12:4539 (1984)], according to specifications provided by the manufacturer. Complementary oligonucleotides are annealed by heating them to 90° C. in a solution of 10 mM Tris-HCl buffer (pH 8.0) containing NaCl (200 mM) and then allowing them to cool slowly to room temperature. For binding and turnover assays, duplex DNA is purified from native polyacrylamide (15% w/v) gels. The band corresponding to double-stranded DNA is excised and soaked overnight in 0.30 M sodium acetate buffer (pH 5.0) containing EDTA (1 mM). After soaking, the supernatant is extracted with phenol/chloroform (1/1 v/v) and precipitated with ethanol. DNA substrates are radiolabeled on their 5'-OH group by treatment with [$\gamma$-$^{32}$P]ATP and T4 polynucleotide kinase. Salts and unincorporated nucleotides are removed by chromatography on Sephadex G columns. Likewise, the cell culture methods described below are also well known in the art.

The present invention relates to the screening of compounds that are agonistic or antagonistic to the mevalonate pathway. Such compounds may be further screened for effectiveness in regulating the production of various end products of the mevalonate pathway. The regulation of these products may be instrumental in the control or treatment of clinical disease states. For example, such compounds may regulate vascular tone and endothelial function including vascular smooth muscle proliferation, plaque stabilization associated with atherosclerotic lesions and associated cholesterol regulation, prevention of glomerular injury in renal disease, treatment of malignancies and prevention of rejection in organ transplant. The current class of drugs, the statins, used for the control of cholesterol levels exert a physiological effect via regulation of the mevalonate pathway. However, these drugs do not all perform equally in terms of modulating cholesterol levels or in other therapeutic properties. In this regard, new drugs or classes of drugs may be more effective for the various therapeutic purposes listed here or for other therapeutic applications.

The present invention is not limited to any particular mechanism or embodiment. In one embodiment, the i$^6$A modification of tRNA catalyzed by Mod5p promotes the efficiency of SUP7 or SUP11 tRNAs in the suppression of UAA nonsense mutations by insertion of tyrosine at positions in the growing peptide corresponding to UAA stop codons (Laten et al., "Isopentenyladenosine deficient tRNA from an antisuppressor mutant of *Saccharomyces cerevisiae*" *Nucleic Acids Res*. 5:4329–4342). The extent to which this nonsense suppression occurs during translation in the cytoplasm, can be used as an indication of the amount of Mod5p and isopentenylated tRNA in the cytoplasm.

The can1-100, ade2-1, and lys2-1 alleles contain UAA nonsense mutations. CAN1 encodes, an arginine permease that allows the uptake of the arginine analog canavanine (Whelan et al., "The CAN1 locus of *Saccharomyces cerevisiae*: fine-structure analysis and forward mutation rates" *Genetics* 91:35–51, 1979). Canavanine interferes with the process of translation and cells can not grow in its presence. Therefore, cells with wild-type CAN1 are sensitive to canavanine (Can$^s$), but cells with the mutant can1-100, that does not encode a properly functioning permease, are resistant to canavanine (Can$^r$) and can grow in its presence. Cells with i$^6$A completely modified SUP7 or SUP11 tRNAs can not grow in the presence of canavanine, whereas cells lacking i$^6$A on these tRNAs are able to grow in the presence of this drug. Cells with intermediate levels of i$^6$A show intermediate levels of growth in the presence of the drug.

ADE2 encodes an enzyme involved in the synthesis of adenine. Cells with ade2-1 turn red in color, due to accumulation of a metabolic intermediate, and fail to grow on defined media lacking adenine (Ade$^-$), while cells producing a functional Ade2p can grow on such media and are white (Ade$^+$) (Rasse-Messenguy and Fink, "Temperature-sensitive nonsense suppressors in yeast" *Genetics* 75:459–464, 1973). Cells with the ade2-1 allele and sufficient i$^6$A modified suppressor tRNA can grow in the absence of exogenous adenine and generate white colonies on rich media whereas cells with insufficient i$^6$A modified suppressor tRNA are unable to grow in the absence of exogenous adenine and generate red colonies on rich media. Cells with intermediate levels of i$^6$A modified tRNA have intermediate phenotypes in colony color and intermediate rates of growth in the absence of exogenous adenine.

LYS2 encodes an enzyme involved in the biosynthesis of lysine. Mutations in this gene prevent growth the on media lacking exogenous lysine. The lys2-1 nonsense allele can be suppressed by SUP7 or SUP11 provided that the encoded nonsense codon suppressing tRNAs possess an i$^6$A modification at position 37. Cells with no Mod5p lack i$^6$A modified tRNA and are unable to grow in the absence of exogenous lysine whereas cells with active cytosolic pools of Mod5p can grow in the absence of this amino acid. Cells with intermediate levels of i$^6$A modified tRNA have intermediate abilities for growth on media lacking lysine.

When a cell contains the wild-type MOD5, encoding both isoforms of Mod5p, the SUP7 or SUP11 pools are fully modified. Such strains efficiently suppress the can1-100, ade2-1 and lys2-1 and they are Can$^s$, Ade$^+$, and Lys$^+$. Cells which have the mutant mod5-1 allele contain approximately 1.5% of the amount of isopentenyl adenosine present in MOD5 cells, so little suppression of can1-100, ade2-1 and lys2-1 will occur, making them Can$^r$, Ade$^-$ and Lys$^-$. Cells with the mod5-M2 allele (strain ALB1, FIG. 2), which contains a mutation at codon 12 preventing the initiation of Mod5p-II translation and allowing only Mod5p-I production, have about 50% of the SUP7 pool modified (FIG. 3) resulting in intermediate levels of suppression. Such cells show intermediate growth on canavanine (Can$^{r/s}$) and on media lacking adenine (Ade$^{+/-}$) and generate pink colonies on rich media. Cells with the mod5-M2KR6 allele (Boguta et al., "Subcellular locations of MOD5 proteins: mapping of sequences sufficient for targeting to mitochondria and demonstration that mitochondrial and nuclear isoforms commingle in the cytosol" *Mol Cell Biol.* 14:2298–2306, 1994; Zoladek et al., "Mutations altering the mitochondrial-cytoplasmic distribution of Mod5p implicate the actin cytoskeleton and mRNA 3' ends and/or protein synthesis in mitochondrial delivery" *Mol Cell Biol* 15:6884–6894, 1995) have a very small cytosolic pool of i$^6$A-tRNA and they are unable to grow in the absence of lysine (FIG. 2).

In the process of searching for genes that caused decreased cytosolic pools of Mod5p-1, ERG20 was found (Benko et al., "Competition between a sterol biosynthetic enzyme and tRNA modification in addition to changes in the protein synthesis machinery causes altered nonsense suppression" *PNAS* 97:61–66, 2000). ERG20 encodes farnesyl diphosphate synthetase. This enzyme catalyzes the formation of geranyl pyrophosphate and farnesyl pyrophosphate by the condensation of units of dimethylallyl pyrophosphate (DMAPP) and its isomer isopentenyl pyrophosphate (IPP). DMAPP is the same molecule used by Mod5p as a substrate in the synthesis of i$^6$A in tRNA (grown and Goldstein, "Multivalent feedback regulation of HMG CoA reductase, a control mechanism coordinating isoprenoid synthesis and cell growth" *J Lipid Res*. 21:505–517, 1980. The applicants proposed that Erg20p over-expression competed for the DMAPP normally channeled to tRNA modification by Mod5p and showed that when Erg20p is highly expressed the level of i$^6$A modification is reduced more than 3-fold. This results show that the mevalonate pathway and the tRNA pathway are in competition and small differences in i$^6$A modification of tRNA that result from competition and flux in the sterol biosynthesis pathway can be detected by simple growth/color assays that score nonsense suppression.

Assays for detecting the ability of agents to inhibit or enhance flux through the mevalonate pathway provide for facile high-throughput screening of agent banks (e.g., compound libraries, peptide libraries, and the like) to identify antagonists or agonists. Such mevalonate pathway antagonists and agonists may be further developed as potential therapeutics and diagnostic or prognostic tools for diverse types of clinical diseases.

1. Screens to Identify Agonists or Antagonists of Mevalonate Pathway Activity

There are several different approaches contemplated by the present invention to look for molecules that specifically are agonistic or antagonistic to the mevalonate pathway.

i Colorimetric Assays

In one embodiment, yeast cells of the stains ALB1 and ALB8 are cultured, exposed to one or more compounds and color is determined visually. In another embodiment, cells are lysed and color is determined with a spectrophotometer.

ii. Growth Assays

In one embodiment, yeast cells of the stains ALB1, ALB8, M14A, T8-1D are cultured, exposed to one or more compounds and growth is determined visually. In another embodiment, cells are suspended in a isotonic solution and cell growth is determined with a spectrophotometer or with a flow cytometer.

iii. Immunoprecipitation and Western Blot

After the generation of antibodies to i⁶A, cells are lysed and then incubated with the antibodies. Antibodies interact with the i⁶A and any associated proteins can then be pulled down with protein-A Sepharose or protein-G Sepharose beads or detected by Western blot, using standard techniques.

EXPERIMENTAL

The following examples are intended to illustrate, but not limit, the present invention. Additionally, the following examples employ standard molecular biological, microbiological and cell culture procedures. These techniques and procedures are generally performed according to conventional methods in the art (see, generally, Sambrook et al. Molecular Cloning: A Laboratory Manual, 2nd ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference).

EXAMPLE 1

Identification of Plasmids Causing Reduced Nonsense Suppression and Sequencing of Inserts of Library Clones The applicants employed the can1-100 and ade2-1 alleles in a mod5-M2 background (strain ALB1) to identify plasmids causing alterations in nonsense suppression. The strains were made as follows: Strain ALB1 (MATα mod5-M2 SUP7 ade2-1 can1-100 leu2-3, -112 lys1-1 lys2-1 trp1 ura3-1) was created from MD14A (Gillman, et al., "MOD5 translation initiation sites determine N6-isopentenyladenosine modification of mitochondrial and cytoplasmic tRNA" *Mol Cell Biol* 14:2298–2306, 1994) by the replacement of the genomic mod5-1 through a pop-in/pop-out procedure (Rothstein, "Targeting, disruption, replacement, and allele rescue: integrative DNA transformation in yeast" *Methods Enzymol* 194:281–301, 1991). Plasmid YCfmod5-M2 (Gillman, et al., "MOD5 translation initiation sites determine N6-isopentenyladenosine modification of mitochondrial and cytoplasmic tRNA" *Mol Cell Biol* 14:2298–2306, 1994) was used as the donor of the M2 mutation. The ARS1 and CEN4 sequences were removed from YCfmod5-M2 by a BglII/SmaI digestion. The BglII end of the remaining plasmid was filled in using Klenow DNA Polymerase, and then ligated to the SmaI blunt end. The resulting plasmid was linearized by SnaBI just upstream of the mod5-M2 ORF and then transformed into MD14A. Integration of the plasmid was selected for by growth on media lacking uracil. Resulting cells contained two mod5 alleles: mod5-1 and mod5-M2. Cells in which intrachromosomal homologous recombination and loss of the mod5-1 mutation occurred were selected for by growth on media containing 5-fluoro-orotic acid (5-FOA), due to concomitant loss of URA3, and for the ability to grow on media lacking adenine. The presence of the remaining mod5-M2 allele was confirmed by DNA blot hybridization.

Strain ALB8 (MATα SUP7 can1-100 ade2-1 leu2-3, -112 lys1-1 lys2-1 trp1 mod5::TRP1 ura3-1::MOD5) was created through integration of a plasmid containing MOD5 at the ura3-1 locus of strain MT-8 (Gillman, et al., "MOD5 translation initiation sites determine N6-isopentenyladenosine modification of mitochondrial and cytoplasmic tRNA" *Mol Cell Biol* 11: 2382–2390, 1991). Plasmid YCfMOD5 (Gillman, et al., "MOD5 translation initiation sites determine N6-isopentenyladenosine modification of mitochondrial and cytoplasmic tRNA" *Mol Cell Biol* 11: 2382–2390, 1991) was used as the donor of MOD5. The ARS1 and CEN4 sequences were removed as described above, and the resulting plasmid was linearized with NcoI to target it to ura3-1. MT-8 cells that acquired the plasmid were selected on media lacking uracil. Correct integrants were assessed by DNA blot hybridization. Strain SL680-9C (MATα asu9-1 sup45-2 ura3-52 can1-132 leu2-1 lys2-1 met8-1 trp1-1 or trp1-289) (Vincent, et al., "The yeast translational allosuppressor, SAL6: a new member of the PP1-like phosphatase family with a long serine-rich N-terminal extension" *Genetics* 138:597–607, 1994) was obtained from S. Liebman.

Yeast strains were propagated in YEPD media or synthetic complete (SC) media lacking certain nutrients to select for the presence of plasmid and to assay suppression. C, Canavanine sulfate salt (SIGMA) was added to media lacking arginine to a final concentration of 30 μg/ml. Yeast strains were transformed following a modified TRAFO protocol (Gietz, et al., "Improved method for high efficiency transformation of intact yeast cells" *Nucleic Acids Res* 20:1425, 1992). Additionally, the following library DNAs and plasmids were used: DNA library based in YEp13 (Nasmyth and Tatchell, "The structure of transposable yeast mating type loci" *Cell* 19:753–764, 1980), a genomic DNA library based in YEp24 (Carlson and Botstein, et al., "Two differentially regulated mRNAs with different 5' ends encode secreted with intracellular forms of yeast invertase" *Cell* 28:145–154, 1982), a cDNA library based in pMac561, a 2 μm vector with the ADH1 promoter (McKnight and McConaughy, "Selection of functional cDNAs by complementation in yeast" *Proc Natl Acad Sci USA* 80:4412–4416) and a cDNA library based in pRS316 (Liu, et al., "Construction of a GAL1-regulated yeast cDNA expression library and its application to the identification of genes whose overexpression causes lethality in yeast" *Genetics* 132:665–673, 1992).

YEpMOD5 contains the 1.8 kb DNA fragment encoding wild-type MOD5 gene and regulatory regions in the YEp24 vector (Dihanich, et al., "Isolation and characterization of MOD5, a gene required for isopentenylation of cytoplasmic and mitochondrial tRNAs of *Saccharomyces cerevisiae*" *Mol Cell Biol* 7:177–184, 1987). pRH127-3, a gift from R. Wright, is a 2 micron-based plasmid that contains a truncated HMG1 gene, that causes increased HMG-CoA reductase activity and increased levels (~10× greater) of intermediates in the mevalonate pathway (Donald, et al., "Effects of overproduction of the catalytic domain of 3-hydroxy-3-methylglutaryl coenzyme A reductase on squalene synthesis in *Saccharomyces cerevisiae*" *Appl Environ Microbiol* 63:3341–3344, 1997).

Library plasmids were isolated from yeast by the method of Ward (Ward, "Single-step purification of shuttle vectors favor yeast for high frequency back-transformation into *E. coli*" *Nucleic Acids Res* 18:5319, 1990). DNAs were sequenced by either the chain termination method (Sanger, et al., "DNA sequencing with chain-terminating inhibitors" *Proc Natl Acad Sci USA* 74:5463–5467, 1977) with Psychognosy Version 2.0 DNA Sequencing Kit United States Biochemical) or by automated cycle sequencing performed in the Pennsylvania State University College of Medicine Macromolecular Core Facility. Nucleotide sequences were identified by a BLAST (Altschul, et al., "Basic local alignment search tool" *J Mol Biol* 215:403–410, 1990) search at the Saccharomyces Genome Database BLAST server [(http://genome-www2.stanford.edu/cgi-bin/SGD/nph-blast2sgd/)].

Mod5-M2 is an allele of MOD5 that encodes normal levels of mitochondrial but reduced levels of cytosolic Mod5p activity. In strains, with this allele cytosolic tRNAs are only partially modified with i$^6$A (60%; Gillman, et al., "MOD5 translation initiation sites determine N6-isopentenyladenosine modification of mitochondrial and cytoplasmic tRNA" *Mol Cell Biol* 11:2382–2390, 1991) and further alterations in Mod5p levels are readily assessed by changes in nonsense suppression (Zoladek, et al., "Mutations altering the mitochondrial-cytoplasmic distribution of Mod5p implicate the actin cytoskeleton and mRNA 3' ends and/or protein synthesis in mitochondrial delivery" *Mol Cell Biol* 15:6884–6894, 1995). The can1-100 and ade2-1 alleles contain UAA nonsense mutations. CAN1 encodes an arginine permease that allows the uptake of the arginine analog canavanine (Whelan, et al., "The CAN1 locus of *Saccharomyces cerevisiae*: fine-structure analysis and forward mutation rates" *Genetics* 91:35–51, 1979), and cells cannot grow in its presence. Therefore, cells with wild-type CAN1 are sensitive to canavanine (Can$^s$), but cells with the mutant can1-100 are resistant to canavanine (Can$^r$). Cells containing SUP7 tRNAs completely modified with i$^6$A have functional arginine permease and, therefore, cannot grow in the presence of canavanine, whereas cells lacking i$^6$A on their tRNAs are able to grow in the presence of this drug. Cells with intermediate levels of i$^6$A show intermediate levels of growth in the presence of the drug.

ADE2 encodes an enzyme involved in the synthesis of adenine. Cells with ade2-1 turn red in color and fail to grow on defined medium lacking adenine (Ade$^-$), whereas cells producing functional Ade2p can grow on such medium (Ade$^+$) and are white (Rasse-Messenguy and Fink, "Temperature-sensitive nonsense suppressors in yeast" *Genetics* 75:459464, 1973). Cells with the ade2-1 allele and sufficient i$^6$A-modified suppressor tRNA can grow in the absence of exogenous adenine and generate white colonies on rich medium, whereas cells with insufficient i$^6$A-modified tRNA are unable to grow in the absence of exogenous adenine and generate red colonies on rich medium. Cells with intermediate levels of i$^6$A modified tRNA have intermediate phenotypes in colony color and intermediate rates of growth in the absence of exogenous adenine.

Transformants able to grow on canavanine were selected from approximately 1.5 million independent ALB1 (relevant genotype: SUP7 ade2-1 can1-100 mod5-M2) transformed cells. One hundred and fifty-eight candidates that exhibited growth on medium containing canavanine were tested for lack of growth on medium lacking adenine to eliminate those gaining canavanine resistance because of additional nonsuppressible mutations in can1-100.

For each of the 71 canavanine-resistant candidates that also were unable to grow well on medium lacking adenine or were red-pink in color, an assay was performed to determine whether these phenotypes required the presence of the library plasmid. Thirty-three candidates showed dependence of suppression levels upon the presence of a plasmid. Analysis of the plasmids in these cells resulted in the identification of 11 with unique restriction patterns. These plasmids were retransformed into ALB1 and the transformants were reassayed for canavanine resistance and adenine prototrophy. One plasmid did not confer either of these phenotypes. Four pRS316 library clones were still able to prevent growth on medium lacking adenine, and six of the remaining clones still could produce both desired phenotypes in ALB1 as confirmed by a second set of co-loss experiments (Table 1). Sequencing of the inserts of these latter 10 clones led to the identification of five different genes: SAL6, ARC1, TEF4, YDL219W, and ERG20.

ERG20, which encodes farnesyl diphosphate synthetase, was found once in each of the YEp13, pMac561, and pRS316 libraries. SAL6 cDNA, encoding a protein phosphatase, was discovered four times in the pRS316 library. ARC1, TEF4, and the putative ORF YDL219w were single candidates from the pRS316 library (Table 1). The pRS316 library is constructed such that the cloned genes are regulated by the GAL1 promoter. Thus, transcription is induced by galactose and repressed by glucose in the media. The effects of the identified genes upon nonsense suppression were dependent on having galactose in the medium (Table 1), showing that the phenotypes are a result of their expression. These clones were used for the examples that follow.

TABLE 1

Growth of Strains Containing Plasmids

| Strain | Growth on canavanine Galactose | Growth/colony color on SC-adenine | |
|---|---|---|---|
| | | Glucose | Galactose |
| MD14A | ++ | −r | −r |
| pRSvector/ALB1 | − | +w | +w |
| pRSSAL6/ALB1 | + | +w | +/−p |
| pRSERG20/ALB1 | + | +w | +/−p |
| pRSARC1/ALB1 | +/− | +w | +/−p |
| pRSYDL219w/ALB1 | +/− | +w | +/−p |
| pRSTEF4/ALB1 | +/− | +w | +/−p |

++, Very strong growth; +, strong growth; +/−, poor growth; −, no growth; r, red; p, pink; w, white.

EXAMPLE 2

SAL6, TEF4, and YDL219w Confer Antisuppressor Phenotypes

SUP45 encodes a translation termination factor, and mutation of this gene can result in omnipotent suppression (Stansfield and Tuite, "Polypeptide chain termination in *Saccharomyces cerevisiae*" *Curr Genet* 25:385–395, 1994; Stansfield, et al., "The products of the SUP45 (eRF1) and SUP35 genes interact to mediate translation termination in *Saccharomyces cerevisiae*" *EMBO J* 14:4365–4373, 1995). When SAL6 is overexpressed in a yeast strain containing sup45-2, an anti-suppressor phenotype occurs (Vincent, et al., "The yeast translational allosuppressor, SAL6: a new member of the PP1-like phosphatase family with a long serine-rich N-terminal extension" *Genetics* 138:597–607, 1994). This suggested that the canavanine resistance conferred upon ALB1 by high levels of Sal6p also may be due to antisuppression. Therefore, all of the candidate genes were tested for effects upon translation by assessing whether they scored as antisuppressors of sup45-2.

SL680-9C (relevant genotype sup45-2 asu1 leu2-1 met8-1 ura3-52) is capable of growing on medium lacking methionine because the mutant sup45 permits translation through nonsense mutations such as met8-1 (Vincent, et al., "The yeast translational allosuppressor, SAL6: a new member of the PP1-like phosphatase family with a long serine-rich N-terminal extension" *Genetics* 138:597–607, 1994; Stansfiel d and Tuite, "Polypeptide chain termination in *Saccharomyces cerevisiae*" *Curr Genet* 25:385–395, 1994; Stansfield, et al., "The products of the SUP45 (eRF1) and SUP35 genes interact to mediate translation termination in *Saccharomyces cerevisiae*" *EMBO J* 14:4365–4373, 1995). When SAL6 is overexpressed in a yeast strain containing sup45-2, an anti-suppressor phenotype occurs (Vincent, et al., "The yeast translational allosuppressor, SAL6: a new member of the PP1-like phosphatase family with a long serine-rich N-terminal extension" *Genetics* 138:597–607, 1994). The asu9 antisuppressor allele serves to weaken the effects of sup45 and permits better growth of cells with both mutations (Vincent, et al., "The yeast translational allosuppressor, SAL6: a new member of the PP1-like phosphatase family with a long serine-rich N-terminal extension" *Genetics* 138:597–607, 1994; Stansfield and Tuite, "Polypeptide chain termination in *Saccharomyces cerevisiae*" *Curr Genet* 25:385–395, 1994).

TABLE 2

Growth of SL680-9C cells overexpressing candidate genes

| Candidate gene/ORF | Growth on SC-uracil-methionine (galactose) | Growth/colony color on SC-adenine (glucose) |
|---|---|---|
| None (vector only) | + | + |
| SAL6 | – | + |
| ARC1 | + | + |
| TEF4 | +/–* | + |
| ERG20 | + | + |
| YDL219w | +/– | + |

Cells were grown at 28° C. for 5–8 days; results are for three experiments.
+, strong growth; +/–, poor growth; –, no growth.
*Galactose vs. glucose growth difference sometimes not apparent.

SL680-9C cells transformed by each of the candidate genes in the pRS316 vector were analyzed for growth on galactose-containing or glucose-containing medium lacking uracil and methionine. The data (Table 2) indicate that overexpressed SAL6 and, to a lesser degree, TEF4 and YDL219w cause antisuppression, and, therefore, loss of suppression of the can1-100 and ade2-1 in ALB1 is likely Mod5p-I-independent. This phenotype was not observed consistently in the cells containing large amounts of Tef4p. Neither Arc1p nor Erg20p in high levels affected the suppression of met8-1 in SL680-9C, and, therefore, each probably affects can1-100 and ade2-1 suppression in ALB1 via another route, likely by alteration of Mod5p-I or tRNA activities or location.

EXAMPLE 3

Overexpression of ERG20 Results in the Reduction of Isopentenyl Adenosine Present in tRNA The protein encoded by ERG20, farnesyl diphosphate synthetase, catalyzes the formation of geranyl pyrophosphate and farnesyl pyrophosphate by the condensation of units of DMAPP and its isomer isopentenyl pyrophosphate (IPP). DMAPP is the same molecule used by Mod5p as a substrate in the synthesis of $i^6A$ in tRNA (FIG. 1; Brown and Goldstein, "Multivalent feedback regulation of HMG CoA reductase, a control mechanism coordinating isoprenoid synthesis and cell growth" *J Lipid Res* 21:505–517, 1980; Voet and Voet, *Biochemistry* (Wiley, NY) 1990). It was possible that the large pool of Erg20p produced from the library clones used the DMAPP normally utilized for tRNA modification. This would cause reduced $i^6A$-modified tRNA and, hence, reduced function of these tRNAs in nonsense suppression. It was also possible that others of the candidate genes, when overexpressed, inhibited the formation of $i^6A$ tRNA.

To determine the effect of overexpression of the candidate genes upon $i^6A$ modification of tRNA, Applicants employed the Mid-western procedure (Rasmussen and Culbertson, "Analysis of yeast trimethylguanosine-capped RNAs by midwestern blotting" *Gene* 182:89–96, 1996) by using anti-$i^6A$ antibody.

Figure 2A:
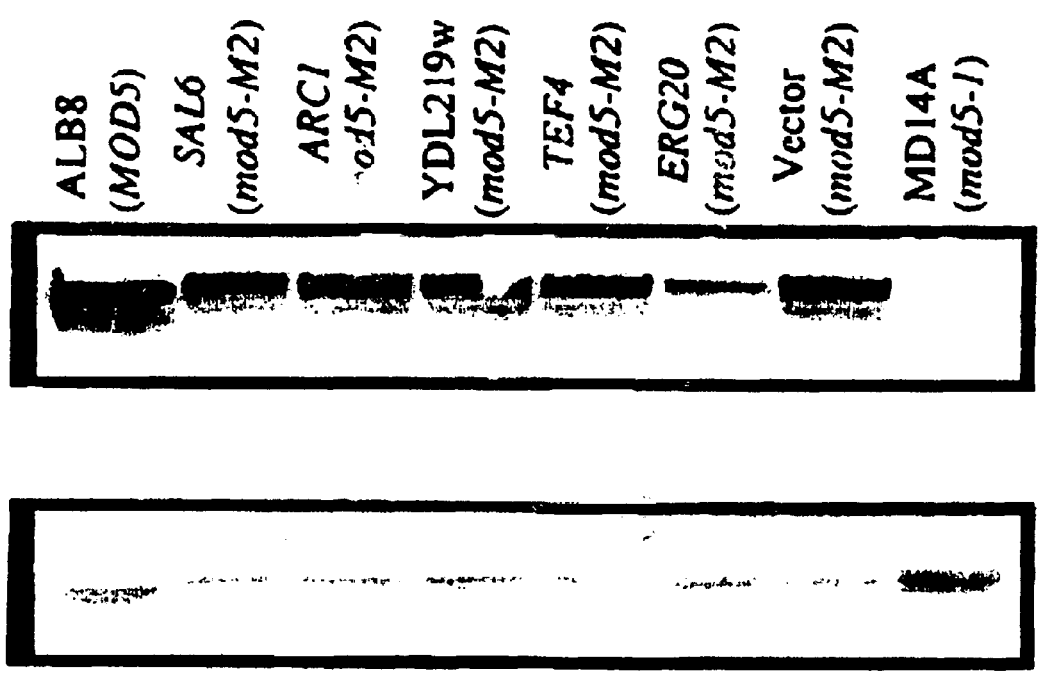
FIG. 2A is an autoradiograph. Low molecular weight RNA was prepared from ALB1 (mod5-M2) with each of the candidate genes or vector alone, ALB8 (MOD5) or MD14A (mod5-1). The RNAs were resolved on polyacrylamide gels, transferred to membranes and probed with anti-isopentenyl adenosine antibody (upper panel) or radiolabeled oligonucleotide complementary to mature tRNA$^{Tyr}$ (lower panel). This autoradiogaph shows the level of isopentenylated tRNA found in ALB1 over-expressing ERG20 is substantially reduced.
Figure 2B:
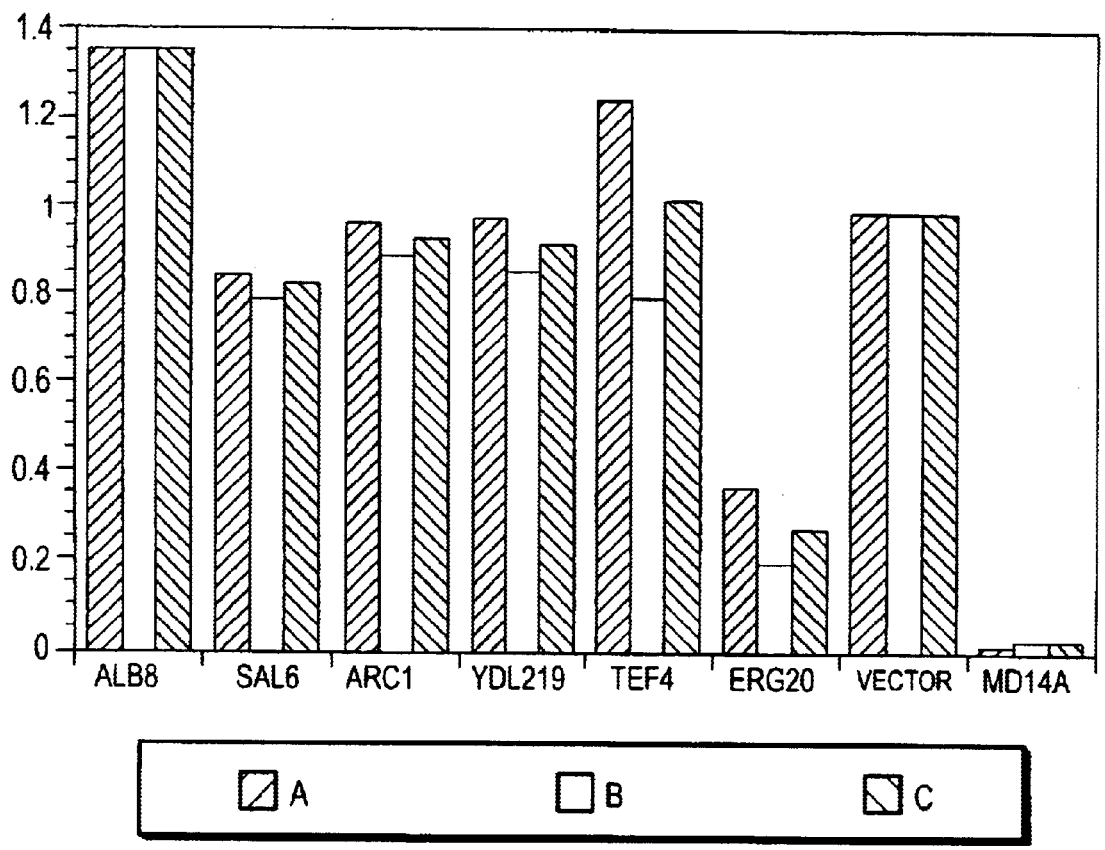
FIG. 2B is a graph. This graph presents data showing the levels of isopentenyl adenosine tRNA found in ALB1 with each of the candidate genes or vector only or in the strain ALB8 or MD14A that were assessed by densitometric analysis of two immunoblots and expressed as a fraction of the level found in the "vector" control. (A) membrane 1 values; (B) membrane 2 values; (C) average values. These data are also consistent with the finding that the level of isopentenylated tRNA found in ALB1 over-expressing ERG20 is substantially reduced.
Figure 3A:
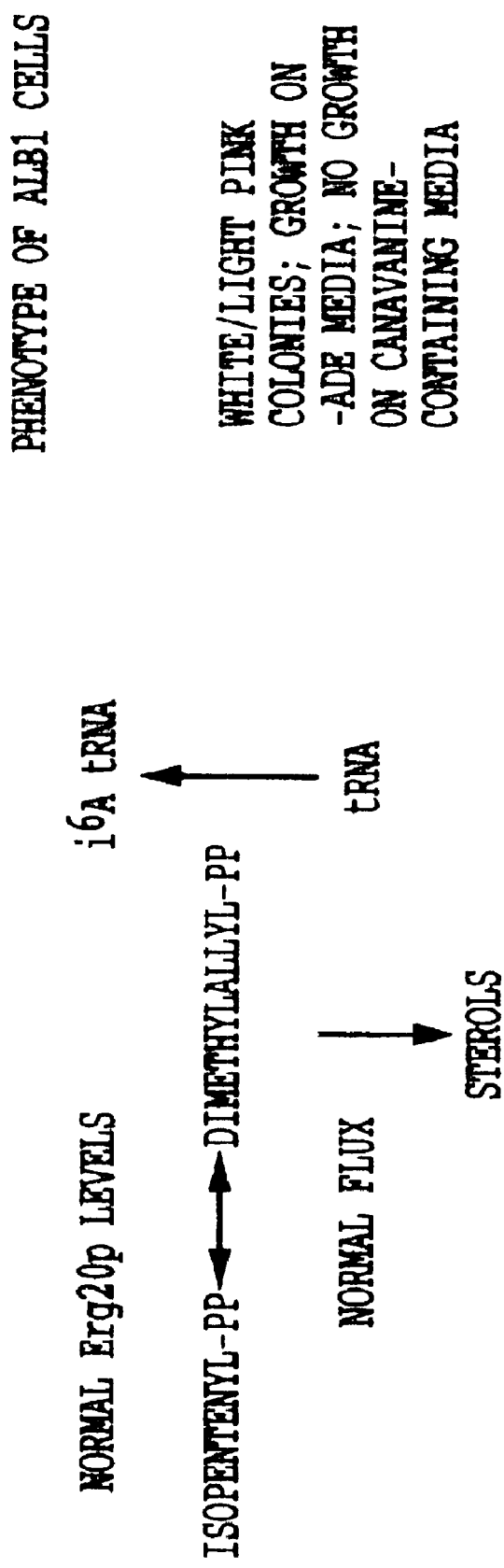
FIG. 3A presents a model of competition between i$^6$A modification of tRNA and sterol biosynthesis.
Figure 3B:
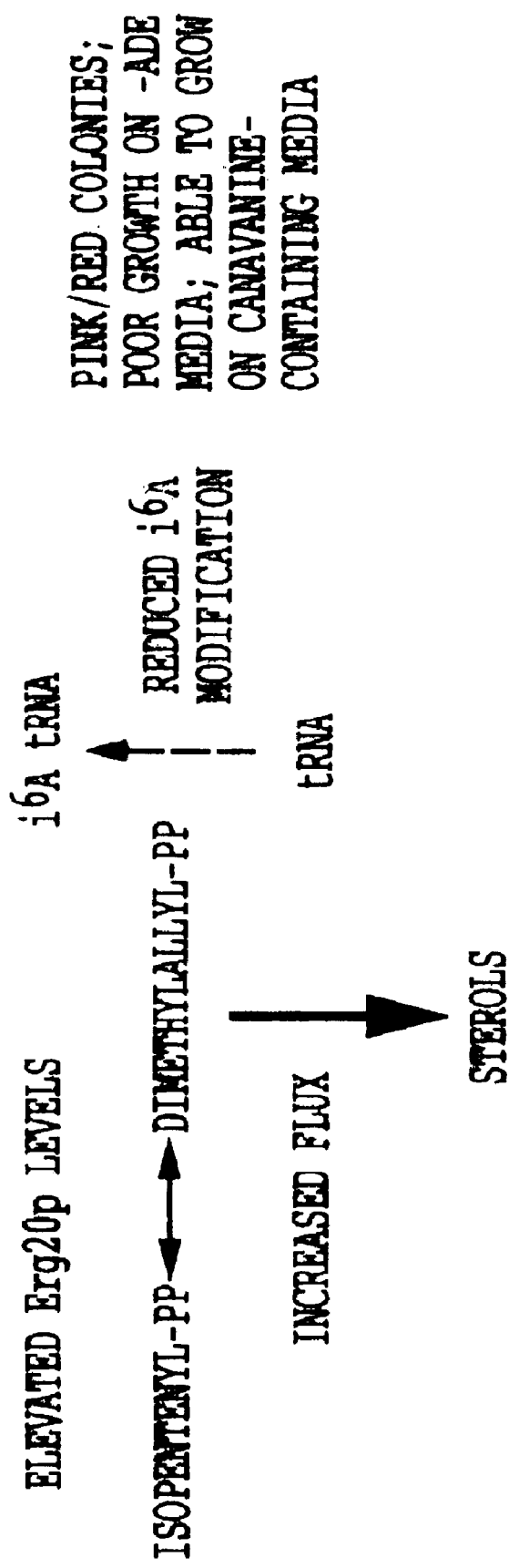
FIG. 3B presents another model of competition between i$^6$A modification of tRNA and sterol biosynthesis.

Low-molecular-weight RNA was prepared from cells with each plasmid and from control strains of ALB1 with vector only, ALB8, and MD14A. The RNAs were resolved on urea-polyacrylamide gels, transferred to membranes, and probed with anti-$i^6A$ antibody (FIG. 2A, upper). Hybridization with a radiolabeled oligonucleotide complementary to part of mature tRNA Tyr was used to assess the relative amount of tRNA in each lane FIG. 2A, lower). Through densitometric analysis, the amount of $i^6A$ formed in tRNA of each strain as a fraction of the amount formed in the vector-only control strain was determined (FIG. 2B).

As expected (Martin and Hopper, "Isopentenylation of both cytoplasmic and mitochondrial tRNA is affected by a single nuclear mutation" *J Biol Chem* 257:10562–10565, 1982), MD14A cells with the mod5-1 allele have barely detectable levels of modified tRNA. Also as anticipated, ALB8 cells with a wild-type MOD5 that encodes both Mod5p-I and Mod5p-II contained higher levels (35% more) of $i^6A$-modified tRNA than ALB1 cells expressing only Mod5p-I (FIG. 2; Gillman, et al. "MOD5 translation initiates sites determine $N^6$-isopentenyladenasine modification of mitochondrial and cytoplasmic tRNA" *Mol Cell Biol* 11:2382–2390, 1991). The level of $i^6A$ tRNA in ALB1 overexpressing SAL6, ARC1, YDL219w, or TEF4 is similar to the level of $i^6A$ from ALB1 cells with vector only. However, the amount of $i^6A$ tRNA in ALB1 with excess Erg20p is significantly reduced to approximately 30% of that in ALB1 with vector alone. Overproduction of Erg20p results in reduced levels of $i^6A$ tRNA and causes a decrease in nonsense suppression.

TABLE 3

Growth of Strains Containing Multicopy Plasmids

| ALB1 with plasmids | Growth on canavanine | Growth/colony color on SC-adenine |
|---|---|---|
| YEp13 + YEpMOD5 | – | +w |
| YEpERG20 + YEp24 | +/– | +/–p |
| YEpERG20 + YEPMODS | – | +w |
| YEp13 + YEp24 | – | +w |
| YEp13 + pRH127-3 | – | +w |
| YEpERG20 + YEp24 | +/– | +/–p |
| YEpERG20 + pRH127-3 | +/– | +w |

+, strong growth; +/–, poor growth; –, no growth; p, pink; w, white.

If overproduction of Erg20p acts via competition with Mod5p-I for a common substrate (FIG. 3), then providing additional Mod5p should reverse the loss of suppression. To test this, Applicants transformed ALB1 cells containing YEpERG20, ERG20 in a multi copy vector, with YEpMOD5 and assessed suppression of ade2-1 and can1-100. The results (Table 3) show that suppression indeed is restored by additional Mod5p. Likewise, if Erg20p and Mod5p are in competition for the same substrate, then alterations that increase the substrate should dampen the competition. To test this, Applicants introduced a multicopy vector harboring a mutant HMG1 gene, pRH127-3, that causes elevated levels of intermediates of the mevalonate pathway (Donald, et al., "Effects of overproduction of the catalytic domain of 3-hydroxy-3-methylglutaryl coenzyme A reductase on squalene synthesis in *Saccharomyces cerevisiae*" *Appl Environ Microbiol* 63:3341–3344, 1997) into ALB1 containing YEpERG20. Applicants found that increased levels of the intermediates also restored nonsense suppression (Table 3). The data support the model that the mevalonate pathway and the i⁶A tRNA modification pathways are in competition.

Determination of the levels of i⁶A in tRNA. RNA was obtained (Hopper, et al., "Processing of intervening sequences: a new yeast mutant which fails to excise intervening sequences from precursor tRNAs" Cell 19:741–751, 1980) from overnight log phase cultures of the following strains: ALB8, MD14A and ALB1 with the pRS316 library plasmids containing SAL6, ARC1, TEF4, ERG20, YDL219w or no cDNA insert. The RNA concentration was calculated from optical density measurement.

RNAs were resolved on a 12% polyacrylamide/7M urea gel. The RNA was transferred to Hybond N+ Nylon Membrane (Amersham) in a Hoefer TE Series Transphor Apparatus containing 1×TAE. The RNA was fixed onto the membrane by UV crosslinking. The membrane was subjected to immunoblotting following the protocol of the Renaissance Western Blot Chemiluminescence Kit (NEN) with slight variation. The primary antibody, anti-i⁶A isolated from rabbit prepared by the method of Senapathy and Jacob (Senapathy and Jacob, "Identification and purification of tRNAs containing N6-(delta 2-isopentenyl) adenosine using antibodies specific for N6-(delta-isopentenyl) adenosine" J Biol Chem 256:11580–11584, 1981), was diluted either 1:33.3 or 1:72.5 prior to use. Horseradish peroxidase conjugated anti-rabbit IgG from donkey (Amersham) diluted 1:5000 or 1:2500 served as secondary antibody. The membrane was also utilized for RNA detection using radiolabeled oligonucleotide complementary to a region of mature tRNA$^{Tyr}$.

The intensities of the fluorescent and radioactive signals for each specimen on the immunoblots and RNA blots, respectively were determined by densitometry using a Molecular Dynamics laser scanner with the Discovery Series Quantity One computer software (Protein Database, Inc.). For each sample, the ratio of its signal with respect to that of the signal from the ALB1 with vector only sample was calculated from the immunoblots (Ratio 1) and from the RNA blots (Ratio 2). The average values for Ratio 1 to Ratio 2 for samples from two membranes were calculated. The data show that increased levels of enzyme activity of the sterol biosynthetic pathway can be assessed indirectly simply by colony color and/or growth on particular medium because changes in nonsense expression occur. Thus, additional mutations and/or drugs that affect the pathway could be identified by the screening protocol described.

EXAMPLE 4

Automated assays

In this experiment yeast cells are cultured as described above in microfiter plates and contact with compounds in order to assess the ability of the compound to modulate the mevalonate pathway. After culture, the cells are lysed in situ and the microtiter plates are analyzed with a manual or automated spectrophotographic plate reader. Attachment of the reader to a computer will allow for the near instantaneous recording and analysis of the data.

Another experiment will utilize automated flow cytometry. In this assay whole cells are analyzed with an automatic sampling flow cytometer calibrated to detect color and/or emitted fluorescence. Additionally, the relative number of cells between samples will be determined to measure cell growth. In any of these examples robotics will be used to analyze a large number of samples quickly.

Downstream products of the mevalonate pathway may be both characterized and quantitated. In addition to the analyses above, effect of the compounds on the mevalonate pathway may be confirmed by analysis of the increased or decreased production of downstream mevalonate pathway products. Such analyses are well known in the art and include radioinmmunoassays (RIA) and high-pressure liquid chromatography (HPLC). In this way, the effected downstream pathway or pathways will be determined.

It should be evident from the foregoing that the present invention provides novel materials and methods that will permit the rapid screening of compounds for their agonistic or antagonistic effect on the mevalonate pathway. In addition, the present invention provides novel materials and methods for the determination of existing or promising therapeutic compounds that may have agonistic or antagonistic side effects on the mevalonate pathway.

---

What is claimed is:

1. A method for screening compounds that are agonistic or antagonistic to the melvalonate pathway in sterol synthesis, comprising:

a) providing: i) a test compound, ii) a growth media lacking arginine and containing a canavanine salt, and iii) modified yeast cells derived from wild type yeast cells, wherein said modified yeast cells express reduced cytosolic activity levels of Mod5p as compared to said wild type yeast cells, and wherein said modified yeast cells comprise a CAN1 gene having a nonsense mutation and a gene coding for a nonsense suppressor tRNA;

b) mixing said growth media and said modified yeast cells to form an untreated modified yeast cell mixture;

c) adding an aliquot of said untreated modified yeast cell mixture in said test compound thereby creating a treated modified yeast cell mixture; and d) measuring the growth of modified yeast cells within said treated modified yeast cell mixture and the growth of modified yeast cells within said untreated yeast cell mixture, wherein a difference in the growth of modified yeast cells within said treated modified yeast cell mixture and the growth of modified yeast cells within said untreated yeast cell mixture indicates the test compound has had an agonistic or antagonistic effect on the melvalonate pathway in sterol synthesis.

2. A method for screening compounds that are agonistic or antagonistic to the melvalonate pathway in sterol synthesis, comprising:

a) providing: i) a test compound, ii) a growth media lacking arginine and containing a canavanine salt, and iii) modified yeast cells derived from wild type yeast cells, wherein said modified yeast cells express reduced cytosolic activity levels of Mod5p as compared to said wild type yeast cells, and wherein said modified yeast cells comprise a CAN1 gene having a nonsense mutation and a SUP7 gene coding for a tRNA;

b) mixing said growth media and said modified yeast cells to form an untreated modified yeast cell mixture;

c) adding an aliquot of said untreated modified yeast cell mixture to said test compound thereby creating a treated modified yeast cell mixture; and d) measuring the growth of modified yeast cells within said treated modified yeast cell mixture and the growth of modified yeast cells within said untreated yeast cell mixture wherein, a difference in the growth of modified yeast cells within said treated modified yeast cell mixture and the growth of modified yeast cells within said untreated yeast cell mixture indicates the test compound has had an agonistic or antagonistic effect on the melvalonate pathway in sterol synthesis.

* * * * *

SEQUENCE LISTING

<160> NUMBER OF SEQ ID NOS: 5

<210> SEQ ID NO 1
<211> LENGTH: 91
<212> TYPE: DNA
<213> ORGANISM: Saccharomyces cerevisiae
<220> FEATURE:
<221> NAME/KEY: CDS
<222> LOCATION: (41)..(91)

<400> SEQUENCE: 1

```
tatacgtaca tatcttttgt aaatagaacc aaaaatcttc atg cta aag gga ccg        55
                                              Met Leu Lys Gly Pro
                                              1               5 ctt aaa ggt tgc tta aat atg tct aaa gaa tgc atg                        91
Leu Lys Gly Cys Leu Asn Met Ser Lys Glu Cys Met
                  10                  15
```

<210> SEQ ID NO 2

-continued

```
<211> LENGTH: 17
<212> TYPE: PRT
<213> ORGANISM: Saccharomyces cerevisiae

<400> SEQUENCE: 2

Met Leu Lys Gly Pro Leu Lys Gly Cys Leu Asn Met Ser Lys Glu Cys
1               5                   10                  15

Met

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
aatcttcaag cttaagggac c                                             21

<210> SEQ ID NO 4
<211> LENGTH: 20
<212> TYPE: DNA
<213> ORGANISM: Artificial Sequence
<220> FEATURE:
<223> OTHER INFORMATION: Synthetic
<221> NAME/KEY: CDS
<222> LOCATION: (1)..(18)

<400> SEQUENCE: 4 ggt tgc tta aat att tct aa                                          20
Gly Cys Leu Asn Ile Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Gly Cys Leu Asn Ile Ser
1               5
```